United States Patent [19]

Klintz et al.

[11] Patent Number: 5,602,074
[45] Date of Patent: Feb. 11, 1997

[54] SUBSTITUTED ISOINDOLONES USEFUL AS PLANT GROWTH REGULATORS

[75] Inventors: Ralf Klintz, Bochum; Elisabeth Heistracher, Ludwigshafen; Peter Schaefer, Bad Durkheim; Gerhard Hamprecht, Weinheim; Uwe Kardorff, Mannheim; Matthias Gerber, Limburgerhof; Karl-Otto Westphalen, Speyer; Helmut Walter, Obrigheim, all of Germany

[73] Assignee: BASF Aktiengesellschaft, Ludwigshafen, Germany

[21] Appl. No.: 343,563

[22] PCT Filed: May 14, 1993

[86] PCT No.: PCT/EP93/01216

§ 371 Date: Nov. 22, 1994

§ 102(e) Date: Nov. 22, 1994

[87] PCT Pub. No.: WO93/24456

PCT Pub. Date: Dec. 9, 1993

[30] Foreign Application Priority Data

May 23, 1992 [DE] Germany .................. 42 17 137.7

[51] Int. Cl.$^6$ ............ C07D 209/46; C07D 209/48; A01N 43/38
[52] U.S. Cl. ............ 504/100; 504/166; 504/225; 504/286; 544/62; 544/144; 548/465; 548/472; 548/473
[58] Field of Search ............ 504/100, 166, 504/255, 286; 544/62, 144; 548/465, 472, 473

[56] References Cited

U.S. PATENT DOCUMENTS 3,992,189 11/1976 Goddard ................... 71/96

5,045,108 9/1991 Elbe et al. ................... 71/94

FOREIGN PATENT DOCUMENTS

| 305333 | 8/1988 | European Pat. Off. . |
| 403891 | 12/1990 | European Pat. Off. . |
| 420810 | 4/1991 | European Pat. Off. . |

OTHER PUBLICATIONS

*Patent Abst. of Japan*, vol. 13, No. 115 (English abstract of JP 63287766) Nov. 1988.
*Patent Abst. of Japan*, vol. 12, No. 252 (English abstract of JP 63039859) Feb. 1988.
*Patent Abst. of Japan*, vol. 13, No. 394 (English abstract of JP 1139580) Jun. 1989.

*Primary Examiner*—Jacqueline Haley
*Attorney, Agent, or Firm*—Keil & Weinkauf

[57] ABSTRACT

Substituted isoindolones I

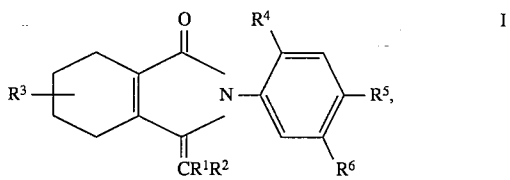

where $R^1$ and $R^2$=H, unsubstituted or substituted alkyl, alkenyl, alkynyl, cyano, $C_1$–$C_6$-alkoxycarbonyl, formyl, $C_1$–$C_6$-alkylcarbonyl, unsubstituted or substituted phenylcarbonyl, $C_3$–$C_8$-cycloalkyl, or, if $R^1$=H, $R^2$ additionally=unsubstituted or substituted phenyl, or $R^1$ and $R^2$, together with the carbon atom to which they are bonded, are an unsubstituted or substituted 3- to 8-membered carbo- or heterocycle;

where $R^3$ to $R^6$ have the meanings given in the specification. The compounds are useful as herbicides and for the desiccation/defoliation of plants.

12 Claims, No Drawings

SUBSTITUTED ISOINDOLONES USEFUL AS PLANT GROWTH REGULATORS

This application is a National Stage Application of PCT/EP93/01216 filed May 14, 1993 and published as WO 93/24456 on Dec. 9, 1993.

The present invention relates to substituted isoindolones of the general formula I

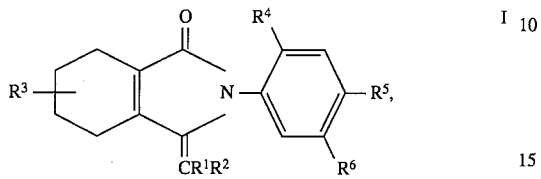

where the variables have the following meanings:

$R^1$ and $R^2$ are
hydrogen, $C_1$–$C_6$-alkyl, $C_2$–$C_6$-alkenyl, $C_2$–$C_6$-alkynyl, tri-($C_1$–$C_6$-alkyl)silyl-$C_2$–$C_6$-alkynyl, $C_1$–$C_6$-alkoxy-$C_1$–$C_6$-alkyl, cyano, $C_1$–$C_6$-cyanoalkyl, $C_1$–$C_6$-alkoxycarbonyl, formyl, $C_1$–$C_6$-alkylcarbonyl, phenylcarbonyl where the phenyl ring can be unsubstituted or can carry one to three radicals selected from a group consisting of $C_1$–$C_6$-alkyl, $C_1$–$C_6$-alkoxy, halogen, cyano, nitro and trifluoromethyl, $C_1$–$C_6$-alkoxycarbonyl-$C_1$–$C_6$-alkyl, $C_1$–$C_6$-alkoxycarbonyl-$C_2$–$C_6$-alkenyl, $C_3$–$C_8$-cycloalkyl or $C_1$–$C_6$-haloalkyl, or, if $R^1$ is hydrogen, $R^2$ is additionally
phenyl which can be unsubstituted or can carry one to three radicals selected from a group consisting of $C_1$–$C_6$-alkyl, $C_1$–$C_6$-alkoxy, halogen, cyano, nitro and trifluoromethyl, or $R^1$ and $R^2$, together with the common C atom to which they are bonded, are a three- to eight-membered saturated or unsaturated non-aromatic carbo- or heterocycle which can carry one to three N atoms and an additional oxygen or sulphur atom and also one or two carbonyl groups, and can be substituted by one to three identical or different $C_1$–$C_6$-alkyl groups;

$R^3$ is
hydrogen or $C_1$–$C_6$-alkyl;

$R^4$ is
hydrogen or halogen;

$R^5$ is
hydrogen, halogen, nitro, cyano or trifluoromethyl;

$R^6$ is
one of the following groups: 3- to 8-membered heterocyclyl which can be saturated or partially or completely unsaturated and can carry one to four heteroatoms, selected from a group consisting of one to four nitrogen atoms, one or two oxygen atoms and one or two sulfur atoms, where the heterocycle can carry one of the following substituents on each substitutable atom: $C_1$–$C_6$-alkyl, $C_2$–$C_6$-alkenyl, halogen, cyano, nitro, $C_1$–$C_6$-haloalkyl, $C_1$–$C_6$-alkoxy or $C_1$–$C_6$-alkoxycarbonyl, or
one of the following groups:
—A—CN, —A—CO—B, —C($R^{10}$)=O, —C($R^{10}$)=S, —C($R^{10}$)=N—$R^{11}$, —C($X^1R^{14}$)($X^2R^{15}$)$R^{10}$, —P($R^{12}$)($R^{13}$)=O, where A is
a $C_1$–$C_4$-alkylene, $C_2$–$C_4$-alkenylene or $C_2$–$C_4$-alkynylene chain which can in each case be unsubstituted or can carry one or two radicals selected from a group consisting of halogen, cyano, $C_1$–$C_6$-alkyl, $C_1$–$C_6$-alkoxycarbonyl and $C_1$–$C_6$-alkylcarbonyl;

B is
hydrogen, $C_1$–$C_6$-alkyl, $C_3$–$C_6$-alkenyl, $C_3$–$C_6$-alkynyl, $C_1$–$C_6$-haloalkyl, $C_3$–$C_8$-cycloalkyl
—$OR^{16}$ or —$SR^{16}$, where $R^{16}$ is
hydrogen, $C_1$–$C_6$-alkyl, $C_3$–$C_6$-alkenyl, $C_3$–$C_6$-alkynyl, $C_3$–$C_8$-cycloalkyl, $C_2$–$C_6$-haloalkyl,
phenyl which can be unsubstituted or can carry one to three radicals selected from a group consisting of $C_1$–$C_6$-alkyl, $C_2$–$C_6$-alkenyl, halogen, cyano, nitro, $C_1$–$C_6$-alkoxy and $C_1$–$C_6$-alkoxycarbonyl, $C_1$–$C_6$-cyanoalkyl, $C_3$–$C_6$-haloalkenyl, $C_1$–$C_6$-alkoxycarbonyl, $C_1$–$C_6$-alkoxy-$C_1$–$C_6$-alkyl, $C_1$–$C_6$-alkoxycarbonyl-$C_1$–$C_6$-alkyl or $C_1$–$C_6$-alkoximino-$C_1$–$C_6$-alkyl;
phenyl which can be unsubstituted or can carry one to three radicals selected from a group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl;
$NR^8R^9$, where $R^8$ and $R^9$ independently of one another are hydrogen, $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl or phenyl which can be unsubstituted or can carry one to three radicals selected from a group consisting of $C_1$–$C_6$-alkyl, $C_2$–$C_6$-alkenyl, halogen, cyano, nitro, $C_1$–$C_6$-alkoxy and $C_1$–$C_8$-alkoxycarbonyl, or where $R^8$ and $R^9$, together with the common nitrogen atom, form a saturated or partially or completely unsaturated 4- to 7-membered ring which can additionally contain one or two further heteroatoms as ring members, selected from a group consisting of nitrogen, oxygen and sulfur;
$C_1$–$C_6$-alkoxy-$C_1$–$C_6$-alkyl, di-($C_1$–$C_6$-alkoxy)-$C_1$–$C_6$-alkyl, $C_1$–$C_6$-alkylthio-$C_1$–$C_6$-alkyl;

$R^{10}$ is
hydrogen or cyano
$C_1$–$C_6$-alkyl, $C_3$–$C_6$-alkenyl, $C_3$–$C_6$-alkynyl,
$C_1$–$C_6$-haloalkyl,
$C_3$–$C_8$-cycloalkyl,
$C_1$–$C_6$-alkoxycarbonyl,
$C_1$–$C_6$-alkoxycarbonyl-$C_1$–$C_6$-alkyl, $R^{11}$ is
hydrogen, $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl,
phenyl which can be unsubstituted or can carry one to three radicals selected from a group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl,
$C_1$–$C_6$-alkoxy-$C_1$–$C_6$-alkyl, hydroxyl,
$C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_8$-cycloalkyl-$C_1$–$C_6$-alkoxy,
$C_1$–$C_6$-alkylcarbonyloxy,
$C_1$–$C_6$-cyanoalkoxy, $C_1$–$C_6$-alkoxy-$C_1$–$C_6$-alkoxy, $C_1$–$C_6$-alkoxycarbonyl-$C_1$–$C_6$-alkoxy, hydroxy-$C_1$–$C_6$-alkoxy, $C_1$–$C_6$-alkylthio-$C_1$–$C_6$-alkoxy, $C_1$–$C_6$-alkylamino-$C_1$–$C_6$-alkoxy, di-($C_1$–$C_6$-alkyl)-amino-$C_1$–$C_6$-alkoxy,
phenyl-$C_1$–$C_6$-alkoxy, phenyl-$C_3$–$C_6$-alkenyloxy or phenyl-$C_3$–$C_6$-alkynyloxy, where in each case one or two methylene groups of the alkoxy, alkenyloxy and alkynyloxy chains can be replaced by oxygen, sulfur and/or a $C_1$–$C_6$-alkylamino chain, and where the phenyl ring can be unsubstituted or can carry one to three substituents selected from a group consisting of $C_1$–$C_6$-alkyl, $C_2$–$C_6$-alkenyl, halogen, cyano, nitro, $C_1$–$C_6$-alkoxy and $C_1$–$C_6$-alkoxycarbonyl, —$NR^8R^9$;

$R^{12}$ and $R^{13}$ are
$C_1$–$C_6$-alkoxy or phenyl which can be unsubstituted or can carry one to three radicals selected from a group consisting of $C_1$–$C_6$-alkyl, $C_1$–$C_6$-haloalkyl, $C_3$–$C_6$-alkenyl, halogen, cyano, nitro, $C_1$–$C_6$-alkoxy and $C_1$–$C_6$-alkoxycarbonyl;

$X^1$ and $X^2$ are oxygen or sulfur;

$R^{14}$ and $R^{15}$ are
$C_1$–$C_6$-alkyl, $C_3$–$C_6$-alkenyl, $C_3$–$C_6$-alkynyl or $C_1$–$C_6$-alkoxy-$C_1$–$C_6$-alkyl or $R^{14}$ and $R^{15}$ together are a two- to four-membered carbon chain which can be unsaturated and which, if desired, can contain a carbonyl group as a ring member, where the carbon chain can be unsubstituted or can carry one to three radicals selected from a group consisting of $C_1$–$C_6$-alkyl, $C_2$–$C_6$-alkenyl, halogen, cyano, nitro, amino, $C_1$–$C_6$-alkoxy, $C_3$–$C_6$-alkenyloxy, $C_3$–$C_6$-alkynyloxy, carboxyl, $C_1$–$C_6$-alkoxycarbonyl, $C_1$–$C_6$-haloalkyl, $C_1$–$C_6$-alkoxy-$C_1$–$C_6$-alkyl, $C_3$–$C_6$-alkenyloxy-$C_2$–$C_6$-alkyl, $C_3$–$C_6$-alkynyloxy-$C_1$–$C_6$-alkyl, $C_1$–$C_6$-hydroxyalkyl and $C_1$–$C_6$-cyanoalkyl;

or $R^5$ and $R^6$ together are a saturated or partially or completely unsaturated three- to five-membered carbon chain which, if desired, can contain one or two oxygen, sulfur or nitrogen atoms and/or a carbonyl group as ring members, and where the chain can be unsubstituted or can in turn carry one or two radicals selected from a group consisting of cyano, nitro, amino, halogen, $C_1$–$C_6$-alkyl, $C_1$–$C_6$-haloalkyl, $C_2$–$C_6$-alkenyl, $C_3$–$C_6$-alkynyl, $C_1$–$C_6$-cyanoalkyl, $C_1$–$C_6$-alkoxycarbonyl-$C_1$–$C_6$-alkyl, phenyl-$C_1$–$C_6$-alkyl and 3- to 8-membered heterocyclyl-$C_1$–$C_6$-alkyl, where the heterocycle can be saturated or partially or completely unsaturated and can carry one to four heteroatoms selected from a group consisting of one to four nitrogen atoms, one or two oxygen atoms and one or two sulfur atoms;

excluding those compounds I in which $R^1$ and $R^2$ are hydrogen and either $R^5$ and $R^6$ together form a substituted chain —CH=CH—NH— or $R^4$ is fluorine and $R^5$ and $R^6$ together are a substituted chain —O—CH$_2$—CO—NH—, and the agriculturally utilizable salts of the compounds I.

The invention additionally relates to novel intermediates of the formula II.

In addition, the invention relates to herbicides and plant growth regulators which contain these compounds as active substances.

EP-A 420,810 discloses herbicidal substituted isoindolones of the formula I':

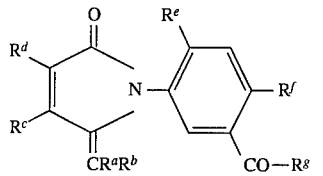

where $R^a$ and $R^b$ are hydrogen, alkyl, unsubstituted or substituted phenyl or, together, are an alkyl-substituted alkylene chain, $R^c$ and $R^d$ are alkyl or, together, are alkyl-substituted tetramethylene, $R^e$ is hydrogen or fluorine, $R^f$ is halogen and $R^g$ is O—W—S(O)$_m$—Q or SAQ1, where W is $C_1$–$C_4$-alkylene, m is 0–2 and Q is alkyl, alkoxyalkyl, alkenyl, alkynyl, cycloalkyl, phenyl or benzyl.

In addition, JA 01/139580 inter alia describes compounds of the formula I"

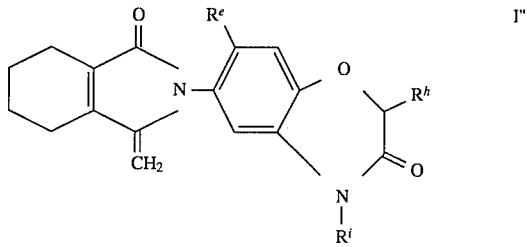

and their use as herbicides, where $R^h$ is hydrogen or alkyl and $R^i$ is substituted O-containing heterocycles, unsubstituted or halogen-substituted alkyl, alkenyl or alkynyl, alkoxyalkyl or alkylthioalkyl.

Additionally, compounds of the formula I'''

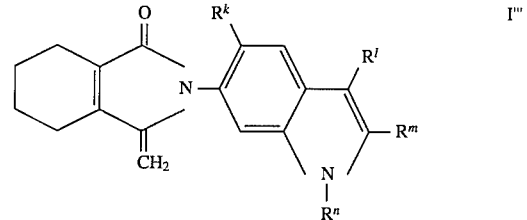

are to be inferred, inter alia, from DE-A 3,924,052, where $R^k$ is hydrogen or halogen, $R^l$ is hydrogen, alkyl or halogen, $R^m$ is hydrogen or alkyl and $R^n$ is hydrogen, unsubstituted or substituted alkyl, alkenyl, alkynyl, cycloalkyl, aralkyl, haloalkyl, alkoxycarbonyl or (di)alkylaminocarbonyl, alkylcarbonyl or alkylsulfonyl.

In addition, JA 88/039859 inter alia discloses herbicidal compounds of the formula I"",

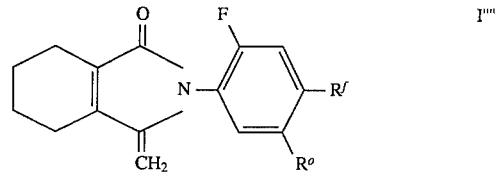

where $R^o$ is, inter alia, hydroxyl, mercapto, phenoxy, alkoxy, hydroxycarbonyl, alkoxycarbonyl, cycloalkoxycarbonyl, alkoxycarbonylalkoxycarbonyl or a carbonate radical.

Other isoindolones are known, for example, from the following publications: EP-A 305,333, EP-A 403,891, U.S. Pat. No. 3,992,189 and JA 03/287,766.

The selectivity of these known herbicides with respect to harmful plants can only be satisfactory, however, in a limited manner, so that it is an object of the present invention to find herbicidal compounds using which (with good tolerability for the crop plants) the harmful plants can be specifically controlled better than hitherto.

We have found that this object is achieved by the substituted isoindolones I defined at the beginning.

In addition, we have found herbicides which contain these substances and have a good herbicidal action.

Additionally, we have found that the compounds I of the invention are suitable as defoliants and desiccants, for example in cotton, potato, rape, sunflowers, soya beans or field beans.

The meanings mentioned above for the substituents $R^1$ to $R^{16}$ are collective terms for individual lists of the single group members. All alkyl, alkenyl, alkynyl, haloalkyl and haloalkoxy moieties can be straight-chain or branched. Haloalkyl and haloalkoxy radicals can carry identical or different halogen atoms.

Specific examples are:

halogen: fluorine, chlorine, bromine and iodine, preferably fluorine and chlorine;

$C_1$–$C_6$-alkyl and the $C_1$–$C_6$-alkyl moieties in the radicals di-($C_1$–$C_6$-alkoxy)-$C_1$–$C_6$-alkyl, $C_1$–$C_6$-alkoxy-$C_1$–$C_6$-alkyl, $C_1$–$C_6$-alkylthio-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-alkoxycarbonyl-$C_1$–$C_6$-alkyl, $C_1$–$C_6$-alkoximino-$C_1$–$C_6$-alkyl, tri-($C_1$–$C_6$-alkyl)silyl-$C_2$–$C_6$-alkynyl and heterocyclyl-$C_1$–$C_6$-alkyl:

methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, isopropyl and tert.-butyl;

$C_2$–$C_6$-alkenyl and the $C_2$–$C_6$-alkenyl moiety in the radical $C_1$–$C_6$-alkoxycarbonyl-$C_2$–$C_6$-alkenyl: ethenyl and $C_3$–$C_6$-alkenyl such as prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably ethenyl and prop-2-en-1-yl;

$C_2$–$C_6$-alkynyl and the $C_2$–$C_6$-alkynyl moiety in the radical tri-($C_1$–$C_6$-alkyl)silyl-$C_2$–$C_6$-alkynyl: ethynyl and $C_3$–$C_6$-alkynyl such as prop-1-in-1-yl, prop-2-in-3-yl;

$C_3$–$C_8$-cycloalkyl and the $C_3$–$C_8$-cycloalkyl moiety in the radical $C_3$–$C_8$-cycloalkyl-$C_1$–$C_6$-alkoxy: cyclopropyl, cyclobutyl, cyclopentyl, cyclohexyl, cycloheptyl and cyclooctyl, preferably cyclopropyl, cyclopentyl and cyclohexyl;

$C_1$–$C_6$-cyanoalkyl: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, and 2-cyanomethylprop-2-yl, preferably cyanomethyl;

$C_1$–$C_6$-haloalkyl: chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_1$–$C_6$-cyanoalkoxy: cyanomethoxy, 1-cyanoeth-1-oxy, 2-cyanoeth-1-oxy, 1-cyanoprop-1-oxy, 2-cyanoprop-1-oxy, 3-cyanoprop-1-oxy, 1-cyanoprop-2-oxy, 2-cyanoprop-2-oxy, 1-cyanobut-1-oxy, 2-cyanobut-1-oxy, 3-cyanobut-1-oxy, 4-cyanobut-1-oxy, 1-cyanobut-2-oxy, 2-cyanobut-2-oxy, 1-cyanobut-3-oxy, 2-cyanobut-3-oxy, 1-cyano-2-methylprop-3-oxy, 2-cyano-2-methylprop-3-oxy, 3-cyano-2-methylprop-3-oxy, and 2-cyanomethylprop-2-oxy, preferably cyanomethoxy;

$C_1$–$C_6$-hydroxyalkoxy: hydroxymethoxy, 1-hydroxyeth-1-oxy, 2-hydroxyeth-1-oxy, 1-hydroxyprop-1-oxy, 2-hydroxyprop-1-oxy, 3-hydroxyprop-1-oxy, 1-hydroxyprop-2-oxy, 2-hydroxyprop-2-oxy, 1-hydroxybut-1-oxy, 2-hydroxybut-1-oxy, 3-hydroxybut-1-oxy, 4-hydroxybut-1-oxy, 1-hydroxybut-2-oxy, 2-hydroxybut-2-oxy, 1-hydroxybut-3-oxy, 2-hydroxybut-3-oxy, 1-hydroxy-2-methylprop-3-oxy, 2-hydroxy-2-methylprop-3-oxy, 3-hydroxy-2-methylprop-3-oxy and 2-hydroxymethylprop-2-oxy, preferably hydroxymethoxy;

phenyl-$C_1$–$C_6$-alkoxy: benzyloxy, 1-phenylethoxy, 2-phenylethoxy, 1-phenylprop-1-oxy, 1-phenylprop-1-oxy, 3-phenylprop-1-oxy, 1-phenylbut-1-oxy, 2-phenylbut-1-oxy, 3-phenylbut-1-oxy, 4-phenylbut-1-oxy, 1-phenylbut-2-oxy, 2-phenylbut-2-oxy, 3-phenylbut-2-oxy, 4-phenylbut-2-oxy, 1-(phenylmethyl)-eth-1-oxy, 1-(phenylmethyl)-1-(methyl)-eth-1-oxy, and 1-(phenylmethyl)-prop-1-oxy, preferably benzyloxy;

$C_1$–$C_6$-alkoxy and the $C_1$–$C_6$-alkoxy moieties in the radicals $C_1$–$C_6$-alkoxy-$C_1$–$C_6$-alkyl, $C_1$–$C_6$-alkylthio-$C_1$–$C_6$-alkyl, $C_3$–$C_7$-cycloalkyl-$C_1$–$C_6$-alkoxy, $C_1$–$C_6$-alkoxy-$C_1$–$C_6$-alkoxy, di-($C_1$–$C_6$-alkoxy)-$C_1$–$C_6$-alkyl, $C_1$–$C_6$-alkylamino-$C_1$–$C_6$-alkoxy and di($C_1$–$C_6$-alkyl)-amino-$C_1$–$C_6$-alkoxy: methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably $C_1$–$C_4$-alkoxy such as methoxy, ethoxy, n-propoxy and n-butoxy;

$C_3$–$C_6$-alkenyloxy and the $C_3$–$C_6$-alkenyloxy moiety in the radical $C_3$–$C_6$-alkenyloxy-$C_1$–$C_6$-alkyl: prop-2-en-1-yloxy, n-buten-4-yloxy, n-buten-3-yloxy, 1-methylprop-2-en-1-yloxy, 2-methylprop-2-en-1-yloxy, n-penten-3-yloxy, n-penten-4-yloxy, n-penten-5-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-2-en-1-yloxy, 1-ethylprop-2-en-1-yloxy, n-hex-2-en-1-yloxy, n-hex-3-en-1-yloxy, n-hex-4-en-1-yloxy, n-hex-5-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut- 2-en-1-yloxy, 1,1-dimethylbut-3-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-3-en-1-yloxy, 2,2-dimethyl-but-3-en-1-yloxy, 2,3-dimethylbut-2-en-1-yloxy, 2,3-dimethylbut-3-en-1-yloxy, 3,3-dimethylbut-2-en-1-yloxy, 1-ethylbut-2-en-1-yloxy, 1-ethylbut-3-en-1-yloxy, 2-ethylbut-2-en-1-yloxy, 2-ethyl-but-3-en-1-yloxy, 1,1,2-trimethylprop-2-en-1-yloxy, 1-ethyl-1-methylprop-2-en-1-yloxy and 1-ethyl-2-methylprop-2-en-1-yloxy, preferably ethenyloxy and prop-2-en-1-yloxy;

$C_3$–$C_6$-alkynyloxy and the $C_3$–$C_6$-alkynyloxy moiety in the radical $C_3$–$C_6$-alkynyloxy-$C_1$–$C_6$-alkyl: prop-1-yn-1-yloxy, prop-2-yn-3-yloxy, n-but-1-yn-4-yloxy, n-but-2-yn-1-yloxy, n-pent-1-yn-3-yloxy, n-pent-1-yn-4-yloxy, n-pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-3-yloxy, 3-methylpent-1-yn-4-yloxy, 3-methylpent-1-yn-5-yloxy, 4-methylpent-2-yn-4-yloxy and 4-methylpent-2-yn-5-yloxy, preferably prop-2-ynyloxy;

$C_3$–$C_6$-haloalkenyl: 2-chloroprop-2-enyl, 3-chloroprop-2-enyl, 2,3-dichloroprop-2-enyl, 3,3-dichloroprop-2-enyl, 2,3,3-trichloroprop-2-enyl, 2,3-dichlorobut-2-enyl, 2-bromoprop-2-enyl, 3-bromoprop-2-enyl, 2,3-dibromoprop-2-enyl, 3,3-dibromoprop-2-enyl, 2,3,3-tribromoprop-2-enyl and 2,3-dibromobut-2-enyl;

$C_3$–$C_6$-haloalkenyloxy: 2-chloroprop-2-enyloxy, 3-chloroprop-2-enyloxy, 2,3-dichloroprop-2-enyloxy, 3,3-dichloroprop-2-enyloxy, 2,3,3-trichloroprop-2-enyloxy, 2,3-dichlorobut-2-enyloxy, 2-bromoprop-2-enyloxy, 3-bromoprop-2-enyloxy, 2,3-dibromoprop-2-enyloxy, 3,3-dibromoprop-2-enyloxy, 2,3,3-tribromoprop-2-enyloxy and 2,3-dibromobut-2-enyloxy;

phenyl-$C_3$–$C_6$-alkenyloxy: 2-phenylprop-2-enyloxy, 3-phenylprop-2-enyloxy, 4-phenylbut-2-en-1-yloxy;

phenyl-$C_3$–$C_6$-alkynyloxy: 3-phenylprop-2-ynyloxy, 4-phenylbut-2-yn-1-yloxy;

$C_5$–$C_7$-cycloalkoxy: cyclopentyloxy, cyclohexyloxy and cycloheptyloxy;

$C_5$–$C_7$-cycloalkenyloxy such as cyclopent-1-enyloxy, cyclopent-2-enyloxy, cyclopent-3-enyloxy, cyclohex-1-enyloxy, cyclohex-2-enyloxy, cyclohex-3-enyloxy, cyclohept-1-enyloxy, cyclohept-2-enyloxy, cyclohept-3-enyloxy and cyclohept-4-enyloxy;

$C_1$–$C_6$-alkylamino in the radical $C_1$–$C_6$-alkylamino-$C_1$–$C_6$-alkoxy: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutylamino, 2,2-dimethylpropylamino, 1-ethylpropylamino, n-hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino and 1-ethyl-2-methylpropylamino, preferably $C_1$–$C_4$-alkylamino such as methylamino, ethylamino, n-propylamino, 1-methylethylamino, n-butylamino, 1-methylpropylamino, 2-methylpropylamino and 1,1-dimethylethylamino, preferably $C_1$–$C_6$-alkylamino-$C_1$–$C_6$-alkoxy such as methylaminomethoxy, ethylaminomethoxy, n-propylaminomethoxy, (1-methylethylamino)methoxy, n-butylaminomethoxy, (1-methylpropylamino)methoxy, (2-methylpropylamino)methoxy, (1,1-dimethylethylamino)methoxy, n-pentylaminomethoxy, (1-methylbutylamino)methoxy, (2-methylbutylamino)methoxy, (3-methylbutylamino)methoxy, (2,2-dimethylpropylamino)methoxy, (1-ethylpropylamino)methoxy, n-hexylaminomethoxy, (1,1-dimethylpropylamino)methoxy, (1,2-dimethylpropylamino)methoxy, (1-methylpentylamino)methoxy, (2-methylpentylamino)methoxy, (3-methylpentylamino)methoxy, (4-methylpentylamino)methoxy, (1,1-dimethylbutylamino)methoxy, (1,2-dimethylbutylamino)methoxy, (1,3-dimethylbutylamino)methoxy, (2,2-dimethylbutylamino)methoxy, (2,3-dimethylbutylamino)methoxy, (3,3-dimethylbutylamino)methoxy, (1-ethylbutylamino)methoxy, (2-ethylbutylamino)methoxy, (1,1,2-trimethylpropylamino)methoxy, (1,2,2-trimethylpropylamino)methoxy, (1-ethyl-1-methylpropylamino)methoxy, (1-ethyl-2-methylpropylamino)methoxy, methylaminoethoxy, ethylaminoethoxy, n-propylaminoethoxy, (1-methylethylamino)ethoxy, n-butylaminoethoxy, (1-methylpropylamino)ethoxy, (2-methylpropylamino)ethoxy, (1,1-dimethylethylamino)ethoxy, n-pentylaminoethoxy, (1-methylbutylamino)ethoxy, (2-methylbutylamino)ethoxy, (3-methylbutylamino)ethoxy, (2,2-dimethylpropylamino)ethoxy, (1-ethylpropylamino)ethoxy, n-hexylaminoethoxy, (1,1-dimethylpropylamino)ethoxy, (1,2-dimethylpropylamino)ethoxy, (1-methylpentylamino)ethoxy, (2-methylpentylamino)ethoxy, (3-methylpentylamino)ethoxy, (4-methylpentylamino)ethoxy, (1,1-dimethylbutylamino)ethoxy, (1,2-dimethylbutylamino)ethoxy, 1,3-dimethylbutylamino)ethoxy, (2,2-dimethylbutylamino)ethoxy, (2,3-dimethylbutylamino)ethoxy, (3,3-dimethylbutylamino)ethoxy, (1-ethylbutylamino)ethoxy, (2-ethylbutylamino)ethoxy, (1-ethylbutylamino)ethoxy, (2-ethylbutylamino)ethoxy, (1,1,2-trimethylpropylamino)ethoxy, (1,2,2-trimethylpropylamino)ethoxy, (1-ethyl-1-methylpropylamino)ethoxy, (1-ethyl-2-methylpropylamino)ethoxy, 2-(methylamino)propoxy, 3-(methylamino)propoxy, 2-(ethylamino)propoxy;

di-($C_1$–$C_6$-alkyl)amino in the radical di-($C_1$–$C_6$-alkyl)amino-$C_1$–$C_6$-alkoxy: N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di(1,1-dimethylethyl)amino, N-ethyl-N-methylamino, N-methyl-N-propylamino, N-methyl-N-(1-methylethyl)amino, N-butyl -N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methyl-ethyl)amino, N-butyl-N-ethylamino, N-ethyl-N-(1-methylpropyl)amino, N-ethyl-N(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably di-$(_1$–$C_2)$-alkylamino-($C_1$–$C_2$)-alkoxy such as N,N-dimethylaminomethoxy, N,N-di-ethylaminomethoxy, N,N -dipropylaminomethoxy, N,N-di-(1-methylethyl)aminomethoxy, N,N-dibutylaminomethoxy, N,N-di-(1-methylpropyl)aminomethoxy, N,N-di-(2-methylpropyl)aminomethoxy, N,N-di-(1,1-dimethylethyl)aminomethoxy, N-ethyl-N-methylaminomethoxy, N-methyl-N-propylaminomethoxy, N-methyl-N-(1-methylethyl)aminomethoxy, N-butyl-N-methylaminomethoxy, N-methyl-N-(1-methylpropyl)aminomethoxy, N-methyl-N-(2-methylpropyl)aminomethoxy, N-(1,1-dimethylethyl)-N-methylaminomethoxy, N-ethyl-N-propylaminomethoxy, N-ethyl-N-(1-methylethyl)aminomethoxy, N-butyl-N-ethylaminomethoxy, N-ethyl-N-(1-methylpropyl)aminomethoxy, N-ethyl-N-(2-methylpropyl)aminomethoxy, N-ethyl-N-(1,1-dimethylethyl)aminomethoxy, N-(1-methylethyl)-N-propylaminomethoxy, N-butyl-N-propylaminomethoxy, N-(1-methylpropyl)-N-propylaminomethoxy, N-(2-methylpropyl)-N-propylaminomethoxy, N-(1,1-dimethylethyl)-N-propylaminomethoxy, N-butyl-N-(1-methylethyl)aminomethoxy, N-(1-methylethyl)-N-(1-methylpropyl)aminomethoxy, N-(1-methylethyl)-N-(2-methylpropyl)aminomethoxy, N-(1,1-dimethylethyl)-N-(1-methylethyl)aminomethoxy, N-butyl-N-(1-methylpropyl)aminomethoxy, N-butyl-N-(2-methylpropyl)aminomethoxy, N-butyl-N-(1,1-dimethylethyl))aminomethoxy, N-(1-methylpropyl)-N-(2-methylpropyl)aminomethoxy, N-(1,1-dimethylethyl)-N-(1-methylpropyl)aminomethoxy, N-(1,1-dimethylethyl)-N-(2-methylpropyl)aminomethoxy, N,N-dimethylaminoethoxy, N,N-diethylaminoethoxy, N,N-di(n-propyl)aminoethoxy, N,N-di(1-methylethyl)aminoethoxy, N,N-dibutylaminoethoxy, N,N-di(1-methylpropyl)aminoethoxy, N,N-di-(2-methylpropyl)aminoethoxy, N,N-di(1,1-dimethylethyl)aminoethoxy, N-ethyl-N-methylaminoethoxy, N-methyl-N-propylaminoethoxy, N-methyl-N-(1-methylethyl)aminoethoxy, N-butyl-N-methylaminoethoxy, N-methyl-N-(1-methylpropyl)aminoethoxy, N-methyl-N-(2-methylpropyl)aminoethoxy, N-(1,1-dimethylethyl)-N-methylaminoethoxy, N-ethyl-N-propylaminoethoxy, N-ethyl-N-(1-methylethyl)aminoethoxy, N-butyl-N-ethylaminoethoxy, N-ethyl-N-(1-methylpropyl)aminoethoxy, N-ethyl-N-(2-methylpropyl)aminoethoxy, N-ethyl-N-(1,1-dimethylethyl)aminoethoxy, N-(1-methylethyl)-N-propylaminoethoxy, N-butyl-N-propylaminoethoxy, N-(1-methylpropyl)-N-propylaminoethoxy, N-(2-methylpropyl)-N-propylaminoethoxy, N-(1,1-dimethylethyl)-N-propylaminoethoxy, N-butyl-N-(1-methylethyl)aminoethoxy, N-(1-methylethyl)-N-(1-methylpropyl)aminoethoxy, N-(1-methylethyl)-N-(2-methylpropyl)aminoethoxy, N-(1,1-dimethylethyl)-N-(1-methylethyl)aminoethoxy, N-butyl-N-(1-methylpropyl)aminoethoxy, N-butyl-N-(2-methylpropyl)aminoethoxy, N-butyl-N-(1,1-dimethylethyl)aminoethoxy, N-(1-methylpropyl)-N-(2-methylpropyl)aminoethoxy, N-(1,1-dimethylethyl)-N-(1-methylpropyl)aminoethoxy, and N-(1,1-dimethylethyl)-N-(2-methylpropyl)aminoethoxy;

$C_1$–$C_6$-alkoxy-$C_1$–$C_6$-alkyl: methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, n-pentoxymethyl, (1-methylbutoxy)methyl, (2-methylbutoxy)methyl, (3-methylbutoxy)methyl, (2,2-dimethylpropoxy)methyl, (1-ethylpropoxy)methyl, n-hexoxymethyl, (1,1-dimethylpropoxy)methyl, (1,2-dimethylpropoxy)methyl, (1-methylpentoxy)methyl, (2-methylpentoxy)methyl, (3-methylpentoxy)methyl, (4-methylpentoxy)methyl, (1,1-dimethylbutoxy)methyl, (1,2-dimethylbutoxy)methyl, (1,3-dimethylbutoxy)methyl, (2,2-dimethylbutoxy)methyl, (2,3-dimethylbutoxy)methyl, (3,3-dimethylbutoxy)methyl, (1-ethylbutoxy)methyl, (2-ethylbutoxy)methyl, (1,1,2-trimethylpropoxy)methyl, (1,2,2-trimethylpropoxy)methyl, (1-ethyl-1-methylpropoxy)methyl, (1-ethyl-2-methylpropoxy)methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy)ethyl, n-pentoxyethyl, (1-methylbutoxy)ethyl, (2-methylbutoxy)ethyl, (3-methylbutoxy)ethyl, (2,2-dimethylpropoxy)ethyl, (1-ethylpropoxy)ethyl, n-hexoxyethyl, (1,1-dimethylpropoxy)ethyl, (1,2-dimethylpropoxy)ethyl, (1-methylpentoxy)ethyl, (2-methylpentoxy)ethyl, (3-methylpentoxy)ethyl, (4-methylpentoxy)ethyl, (1,1-dimethylbutoxy)ethyl, (1,2-dimethylbutoxy)ethyl, (1,3-dimethylbutoxy)ethyl, (2,2-dimethylbutoxy)ethyl, (2,3 -dimethylbutoxy)ethyl, (3,3-dimethylbutoxy) ethyl, (1-ethylbutoxy)ethyl, (2-ethylbutoxy)ethyl, (1,1,2-trimethylpropoxy)ethyl, (1,2,2-trimethylpropoxy)ethyl, 1-(ethyl-1-methylpropoxy)ethyl, (1-ethyl-2-methylpropoxy)ethyl, 2-(methoxy)propyl, 3-(methoxy)propyl, 2-(ethoxy)propyl;

$C_1$–$C_6$-alkylthio-$C_1$–$C_6$-alkyl: methylthiomethyl, ethylthiomethyl, n-propylthiomethyl, (1-methylethylthio)methyl, n-butylthiomethyl, (1-methylpropylthio)methyl, (2-methylpropylthio)methyl, (1,1- dimethylethylthio) methyl, m-pentylthiomethyl, (1-methylbutylthio) methyl, (2-methylbutylthio)methyl, (3-methylbutylthio)methyl, (2,2-dimethylpropylthio)methyl, (1-ethylpropylthio)methyl, n-hexylthiomethyl, (1,1-dimethylpropylthio)methyl, (1,2-dimethylpropylthio)methyl, (1-methylpentylthio)methyl, (2-methylpentylthio)methyl, (3-methylpentylthio, methyl, (4-methylpentylthio)methyl, (1,1-dimethylbutylthio)methyl, (1,2-dimethylbutylthio)methyl, (1,3-dimethylbutylthio)methyl, (2,2-dimethylbutylthio)methyl, (2,3-dimethylbutylthio)methyl, (3,3-dimethylbutylthio)methyl, (1-ethyl butylthio)methyl, (2-ethylbutylthio)methyl, (1,1,2-trimethylpropylthio)methyl, (1,2,2-trimethylpropylthio)methyl, (1-ethyl-1-methylpropylthio)methyl, (1-ethyl-2-methylpropylthio)methyl, methylthioethyl, ethylthioethyl, n-propylthioethyl, (1-methylethylthio) ethyl, n-butylthioethyl, (1-methylpropylthio)ethyl, (2-methylpropylthio)ethyl, (1,1-dimethylethylthio)ethyl, n-pentylthioethyl, (1-methylbutylthio)ethyl, (2-methylbutylthio)ethyl, (3-methylbutylthio)ethyl, (2,2-dimethylpropylthio)ethyl, (1-ethylpropylthio)ethyl, n-hexylthioethyl, (1,1-dimethylpropylthio)ethyl, (1,2-dimethylpropylthio)ethyl, (1-methylpentylthio)ethyl, (2-methylpentylthio)ethyl, (3-methylpentylthio)ethyl, (4-methylpentylthio)ethyl, (1,1-dimethylbutylthio) ethyl, (1,2-dimethylbutylthio)ethyl, (1,3-dimethylbutylthio)ethyl, (2,2-dimethylbutylthio)ethyl, (2,3-dimethylbutylthio)ethyl, (3,3-dimethylbutylthio) ethyl, (1-ethylbutylthio)ethyl, (2- ethylbutylthio)ethyl, (1,1,2-trimethylpropylthio)ethyl, (1,2,2-trimethylpropylthio) ethyl, (1-ethyl-1-methylpropylthio)ethyl, (1-ethyl-2-methylpropylthio)ethyl, 2-(methylthio)propyl, 3-(methylthio)propyl, 2-(ethylthio)propyl;

$C_1$–$C_6$-alkoximino in the radical $C_1$–$C_6$-alkoximino-$C_1$–$C_6$-alkyl: methoximino, ethoximino, n-propoximino, 1-methylethoximino, n-butoximino, 1-methylpropoximino, 2-methylpropoximino, 1,1-dimethylethoximino, n-pentoximino, 1-methylbutoximino, 2-methylbutoximino, 3-methylbutoximino, 1,1-dimethylpropoximino, 1,2-dimethylpropoximino, 2,2-dimethylpropoximino, 1-ethylpropoximino, n-hexoximino, 1-methylpentoximino, 2-methylpentoximino, 3-methylpentoximino, 4-methylpentoximino, 1,1-dimethylbutoximino, 1,2-dimethylbutoximino, 1,3-dimethylbutoximino, 2,2-dimethylbutoximino, 2,3-dimethylbutoximino, 3,3-dimethylbutoximino, 1-ethylbutoximino, 2-ethylbutoximino, 1,1,2-trimethylpropoximino, 1,2,2-trimethylpropoximino, 1-ethyl-1-methylpropoximino and 1-ethyl-2-methylpropoximino, preferably methoximinomethyl, ethoximinomethyl, n-propoximinomethyl, (1-methylethoximino)methyl, n-butoximinomethyl, (1-methylpropoximino)methyl, (2-methylpropoximino)methyl, (1,1-dimethylethoximino)methyl, n-pentoximinomethyl, (1-methylbutoximino)methyl, (2-methylbutoximino)methyl, (3-methylbutoximino)methyl, 2,2-dimethylpropoximino)methyl, (1-ethylpropoximino)methyl, n-hexoximinomethyl, (1,1-dimethylpropoximino)methyl, (1,2-dimethylpropoximino)methyl, (1-methylpentoximino)methyl, (2-methylpentoximino)methyl, (3-methylpentoximino)methyl, (4-methylpentoximino)methyl, (1,1-dimethylbutoximino)methyl, (1,2-dimethylbutoximino)methyl, (1,3-dimethylbutoximino)methyl, (2,2-dimethylbutoximino)methyl, (2,3-dimethylbutoximino)methyl, (3,3-dimethylbutoximino)methyl, (1-ethylbutoximino)methyl, (2-ethylbutoximino)methyl, (1,1,2-trimethylpropoximino)methyl, (1,2,2-trimethylpropoximino)methyl, (1-ethyl-1-methylpropoximino)methyl, (1-ethyl-2-methylpropoximino)methyl, methoximinoethyl, ethoximinoethyl, n-propoximinoethyl, (1-methylethoximino)ethyl, n-butoximinoethyl, (1-methylpropoximino)ethyl, (2-methylpropoximino)ethyl, (1,1-dimethylethoximino)ethyl, n-pentoximinoethyl, (1-methylbutoximino)ethyl, (2-methylbutoximino)ethyl, (3-methylbutoximino)ethyl, (2,2-dimethylpropoximino)ethyl, (1-ethylpropoximino)ethyl, n-hexoximino-ethyl, (1,1-dimethylpropoximino)ethyl, (1,2-dimethylpropoximino)ethyl, (1-methylpentoximino)ethyl, (2-methylpentoximino) ethyl, (3-methylpentoximino)ethyl, (4-methylpentoximino)ethyl, (1,1-dimethylbutoximino)ethyl, (1,2-dimethylbutoximino)ethyl, (1,3-dimethylbutoximino)ethyl, (2,2-dimethylbutoximino)ethyl, (2,3-dimethylbutoximino)ethyl, (3,3-dimethylbutoximino)ethyl, (1-ethylbutoximino)ethyl, (2-ethylbutoximino)ethyl, (1,1,2-trimethylpropoximino)ethyl, (1,2,2-trimethylpropoximino)ethyl, (1-ethyl-1-methylpropoximino)ethyl, (1-ethyl-2-methylpropoximino)ethyl, 2-(methoximino)propyl, 3-(methoximino)propyl, 2-(ethoximino)propyl, preferably $C_1$–$C_6$-alkoximino-$C_1$–$C_2$-alkyl such as methoximinomethyl, ethoximinomethyl, 2-methoximinoethyl and 2-ethoximinoethyl;

$C_1$–$C_6$-alkoxy-$C_1$–$C_6$-alkoxy: methoxymethoxy, ethoxymethoxy, n-propoxymethoxy, (1-methylethoxy)methoxy, n-butoxymethoxy, (1-methylpropoxy)methoxy, (2-methylpropoxy)methoxy, (1,1-dimethylethoxy)methoxy, n-pentoxymethoxy, (1-methylbutoxy)methoxy, (2-methylbutoxy)methoxy, (3-methylbutoxy)methoxy, (2,2-dimethylpropoxy)methoxy, (1-ethylpropoxy)methoxy, n-hexoxymethoxy, (1,1-dimethylpropoxy)methoxy, (1,2-dimethylpropoxy)methoxy, (1-methylpentoxy)methoxy, (2-methylpentoxy)methoxy, (3-methylpentoxy)methoxy, (4-methylpentoxy)methoxy, (1,1-dimethylbutoxy)methoxy, (1,2-dimethylbutoxy)methoxy, (1,3-dimethylbutoxy)methoxy, (2,2-dimethylbutoxy)methoxy, (2,3-dimethylbutoxy)methoxy, (3,3-dimethylbutoxy)methoxy, (1-ethylbutoxy)methoxy, (2-ethylbutoxy)methoxy, (1,1,2-trimethylpropoxy)methoxy, (1,2,2-trimethylpropoxy)methoxy, (1-ethyl-1-methylpropoxy)methoxy, (1-ethyl-2-methylpropoxy)methoxy, methoxyethoxy, ethoxyethoxy, n-propoxyethoxy, (1-methylethoxy)ethoxy, n-butoxyethoxy, (1-methylpropoxy)ethoxy, (2-methylpropoxy)ethoxy, (1,1-dimethylethoxy)ethoxy, n-pentoxyethoxy, (1-methylbutoxy)ethoxy, (2-methylbutoxy)ethoxy, (3-methylbutoxy)ethoxy, (2,2-dimethylpropoxy)ethoxy, (1-ethylpropoxy)ethoxy, n-hexoxyethoxy, (1,1-dimethylpropoxy)ethoxy, (1,2-dimethylpropoxy)ethoxy, (1-methylpentoxy)ethoxy, (2methylpentoxy)ethoxy, (3-methylpentoxy)ethoxy, (4methylpentoxy)ethoxy, (1,1-dimethylbutoxy)ethoxy, (1,2-dimethylbutoxy)ethoxy, (1,3-dimethylbutoxy) ethoxy, (2,2-dimethylbutoxy)ethoxy, (2,3-dimethylbutoxy)ethoxy, (3,3-dimethylbutoxy)ethoxy, (1-ethylbutoxy)ethoxy, (2-ethylbutoxy)ethoxy, (1,1,2-trimethylpropoxy)ethoxy, (1,2,2-trimethylpropoxy)ethoxy, (1-ethyl-1-methylpropoxy)ethoxy, (1-ethyl-2-methylpropoxy)ethoxy, 2-(methoxy)propoxy, 3-(methoxy)propoxy, 2-(ethoxy)propoxy, preferably $C_1$–$C_6$-alkoxy-$C_1$–$C_6$-alkoxy such as methoxymethoxy, ethoxymethoxy, 2-methoxyethyl and 2-ethoxyethyl;

$C_1$–$C_6$-alkylthio-$C_1$–$C_6$-alkoxy: methylthiomethoxy, ethylthiomethoxy, n-propylthiomethoxy, (1-methylethylthio)methoxy, n-butylthiomethoxy, (1-methylpropylthio)methoxy, (2-methylpropylthio)methoxy, (1,1-dimethylethylthio)methoxy, n-pentylthiomethoxy, (1-methylbutylthio)methoxy, (2-methylbutylthio)methoxy, (3-methylbutylthio)methoxy, (2,2-dimethylpropylthio)methoxy, (1-ethylpropylthio)methoxy, n-hexylthiomethoxy, (1,1-dimethylpropylthio)methoxy, (1,2-dimethylpropylthio)methoxy, (1-methylpentylthio)methoxy, (2-methylpentylthio)methoxy, (3-methylpentylthio)methoxy, (4-methylpentylthio)methoxy, (1,1-dimethylbutylthio)methoxy, (1,2-dimethylbutylthio)methoxy, (1,3-dimethylbutylthio)methoxy, (2,2-dimethylbutylthio)methoxy, (2,3-dimethylbutylthio)methoxy, (3,3-dimethylbutylthio)methoxy, (1-ethylbutylthio)methyl, (2-ethylbutylthio)methoxy, (1,1,2-trimethylpropylthio)methoxy, (1,2,2-trimethylpropylthio)methoxy, (1-ethyl-1-methylpropylthio)methoxy, (1-ethyl-2-methylpropylthio)methoxy, methylthioethoxy, ethylthioethoxy, n-propylthioethoxy, (1-methylethylthio)ethoxy, n-butylthioethoxy, (1-methylpropylthio)ethoxy, (2-methylpropylthio)ethoxy, (1,1-dimethylethylthio)ethoxy, n-pentylthioethoxy, (1-methylbutylthio)ethoxy, (2-methylbutylthio)ethoxy, (3-methylbutylthio)ethoxy, (2,2-dimethylpropylthio)ethoxy, (1-ethylpropylthio)ethoxy, n-hexylthioethoxy, (1,1-dimethylpropylthio)ethoxy, (1,2-dimethylpropylthio)ethoxy, (1-methylpentylthio)ethoxy, (2-methylpentylthio)ethoxy, (3-methylpentylthio)ethoxy, (4-methylpentylthio)ethoxy, (1,1-dimethylbutylthio)ethoxy, (1,2-dimethylbutylthio)ethoxy, (1,3-dimethylbutylthio)ethoxy, (2,2-dimethylbutylthio)ethoxy, (2,3-dimethylbutylthio)ethoxy, (3,3-dimethylbutylthio)ethoxy, (1-ethylbutylthio)ethoxy, (2-ethylbutylthio)ethoxy, (1,1,2-trimethylpropylthio)ethoxy, (1,2,2-trimethylpropylthio)ethoxy, (1-ethyl-1-methylpropylthio)ethoxy, (1-ethyl-2-methylpropylthio)ethoxy, 2-(methylthio)propoxy, 3-(methylthio)propoxy, 2-(ethylthio)propoxy, preferably $C_1$–$C_6$-alkylthio-$C_1$–$C_2$-alkoxy such as methylthiomethoxy, ethylthiomethoxy, 2-methylthioethyl and 2-ethylthioethyl;

$C_1$–$C_6$-alkylcarbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropoxycarbonyl, preferably $C_1$–$C_4$-alkylcarbonyl such as methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl;

$C_1$–$C_6$-alkylcarbonyloxy: methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy and 1-ethyl-2-methylpropoxycarbonyloxy, preferably $C_1$–$C_4$-alkylcarbonyloxy such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, and 1,1-dimethylethylcarbonyloxy;

$C_1$–$C_6$-alkoxycarbonyl and the $C_1$–$C_6$-alkoxycarbonyl moieties in the radicals $C_1$–$C_6$-alkoxycarbonyl-$C_1$–$C_6$-alkyl, $C_1$–$C_6$-alkoxycarbonyl-$C_2$–$C_6$-alkenyl and $C_1$–$C_6$-alkoxycarbonyl-$C_2$–$C_6$-alkoxy:methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentoxycarbonyl, 1-methylbutoxycarbonyl, 2-methylbutoxycarbonyl, 3-methylbutoxycarbonyl, 1,1-dimethylpropoxycarbonyl, 1,2-dimethylpropoxycarbonyl, 2,2-dimethylpropoxycarbonyl, 1-ethylpropoxycarbonyl, n-hexoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropylcarbonyl, preferably such as $C_1$–$C_4$-alkoxycarbonyl such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl;

$C_1$–$C_6$-alkoxycarbonyl-$C_1$–$C_6$-alkyl: methoxycarbonylmethyl, ethoxycarbonylmethyl, n-propoxycarbonylmethyl, (1-methylethoxycarbonyl)methyl, n-butoxycarbonylmethyl, (1-methylpropoxycarbonyl)methyl, (2-methylpropoxycarbonyl)methyl, (1,1-dimethylethoxycarbonyl)methyl, n-pentoxycarbonylmethyl, (1-methylbutoxycarbonyl)methyl, (2-methylbutoxycarbonyl)methyl, (3-methylbutoxycarbonyl)methyl, (1,1-dimethylpropoxycarbonyl)methyl, (1,2-dimethylpropoxycarbonyl)methyl, (2,2-dimethylpropoxycarbonyl)methyl, (1-ethylpropoxycarbonyl)methyl, n-hexoxycarbonylmethyl, (1-methylpentoxycarbonyl)methyl, (2-methylpentoxycarbonyl)methyl, (3-methylpentoxycarbonyl)methyl, (4-methylpentoxycarbonyl)methyl, (1,1-dimethylbutoxycarbonyl)methyl, (1,2-dimethylbutoxycarbonyl)methyl, (1,3-dimethylbutoxycarbonyl)methyl, (2,2-dimethylbutoxycarbonyl)methyl, (2,3-dimethylbutoxycarbonyl)methyl, (3,3-dimethylbutoxycarbonyl)methyl, (1-ethylbutoxycarbonyl)methyl, (2-ethylbutoxycarbonyl)methyl, (1,1,2-trimethylpropoxycarbonyl)methyl, (1,2,2-trimethylpropoxycarbonyl)methyl, (1-ethyl-1-methylpropoxycarbonyl)methyl, (1-ethyl-2-methylpropylcarbonyl)methyl, methoxycarbonylethyl, ethoxycarbonylethyl, n-propoxycarbonylethyl, (1-methylethoxycarbonyl)ethyl, n-butoxycarbonylethyl, (1-methylpropoxycarbonyl)ethyl, (2-methylpropoxycarbonyl)ethyl, (1,1-dimethylethoxycarbonyl) ethyl, n-pentoxycarbonylethyl, (1-methylbutoxycarbonyl)ethyl, (2-methylbutoxycarbonyl) ethyl, (3-methylbutoxycarbonyl)ethyl, (1,1-dimethylpropoxycarbonyl) ethyl, (1,2-dimethylpropoxycarbonyl)ethyl, (2,2-dimethylpropoxycarbonyl)ethyl, (1-ethylpropoxycarbonyl)ethyl, n-hexoxycarbonylethyl, (1-methylpentoxycarbonyl)ethyl, (2-methylpentoxycarbonyl)ethyl, (3-methylpentoxycarbonyl)ethyl, (4-methylpentoxycarbonyl)ethyl, (1,1-dimethylbutoxycarbonyl)ethyl, (1,2-dimethylbutoxycarbonyl) ethyl, (1,3-dimethylbutoxycarbonyl)ethyl, (2,2)dimethylbutoxycarbonyl)ethyl, (2,3-dimethylbutoxycarbonyl)ethyl, (3,3-dimethylbutoxycarbonyl)ethyl, (1-ethylbutoxycarbonyl)ethyl, (2-ethylbutoxycarbonyl) ethyl, (1,1,2-trimethylpropoxycarbonyl)ethyl, (1,2,2-trimethylpropoxycarbonyl)ethyl, (1-ethyl-1-methylpropoxycarbonyl)ethyl, (1-ethyl-2-methylpropylcarbonyl)ethyl, 3-(methoxycarbonyl)propyl, 2-(methoxycarbonyl)propyl and 2-(ethoxycarbonyl)propyl, preferably $C_1$–$C_4$-alkoxycarbonyl-$C_1$–$C_2$-alkyl such as methoxycarbonylmethyl, ethoxycarbonylmethyl, 2-methoxycarbonylethyl and 2-ethoxycarbonylethyl;

a heterocyclyl group and the heterocyclyl radical in the heterocyclyl-$C_1$–$C_6$-alkyl group, where the heterocycle can in each case be saturated or partially or completely unsaturated and can carry one to four heteroatoms: tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,3,4-oxadiazolidinyl, 1,2,4-thiadiazolidinyl, 1,3,4- thiadiazolidinyl, 1,2,4-triazolidinyl, 1,3,4-triazolidin-2-yl, 2,3-dihydrofuryl, 2,4-dihydrofuryl, 2,3-dihydrothienyl, 2,4-dihydrothienyl, 2,3-pyrrolin- 2-yl, 2,4-pyrrolinyl, 2,3-isoxazolinyl, 3,4-isoxazolinyl, 4,5-isoxazolinyl, 2,3-isothiazolinyl, 3,4-isothiazolinyl, 4,5-isothiazolinyl, 2,3-dihydropyrazolyl, 3,4-dihydropyrazolyl, 4,5-dihydropyrazol-1-yl, 2,3-dihydrooxazolyl, 3,4-dihydrooxazolyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl; furanyl, thienyl, pyrrolyl, isoxazolyl, isothiazolyl, pyrazolyl, oxazolyl, thiazolyl, imidazolyl, 1,2,4-oxadiazolyl, 1,3,4-oxadiazolyl, 1,2,4-thiadiazolyl, 1,3, 4-thiadiazolyl, 1,2,4-triazolyl, 1,3,4-triazolyl, pyridinyl, pyridazinyl, pyrimidinyl, pyrazinyl, 1,2,4-triazinyl, 1,3,5-triazinyl, dihydropyran-2-yl, dihydropyran-3-yl, dihydropyran-4-yl, dihydrothiopyran-2-yl, dihydrothiopyran-3-yl, dihydrothiopyran-4-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl,

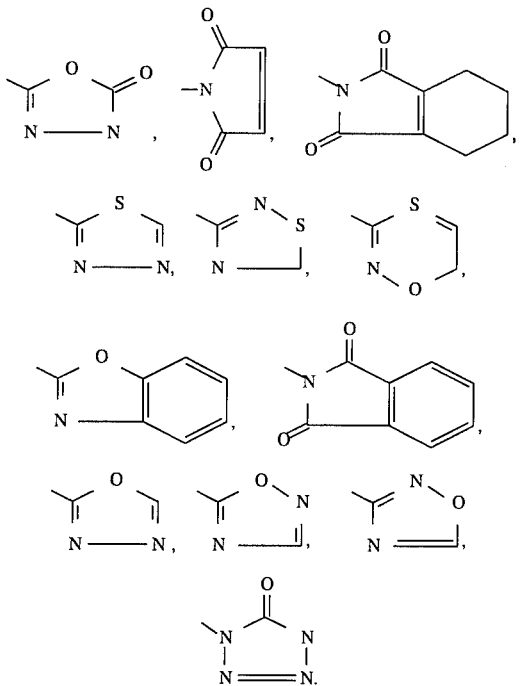

The substituted isoindolones I can be present in the form of their agriculturally utilizable salts, the type of salt generally being unimportant. Suitable salts are usually the salts of those bases which do not have an adverse effect on the herbicidal action of I.

Suitable basic salts are particularly those of the alkali metals, preferably the sodium and potassium salts, those of the alkaline earth metals, preferably calcium, magnesium and barium salts, and those of the transition metals, preferably manganese, copper, zinc and iron salts, as well as the ammonium salts which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, the phosphonium salts, the sulfonium salts, preferably tri-($C_1$–$C_4$)-alkylsulfonium salts, and the sulfoxonium salts, preferably tri-($C_1$–$C_4$)-alkylsulfoxonium salts.

In respect of the use of the isoindolones I of the invention as compounds which have herbicidal and defoliant/desiccant activity, the variables preferably have the following meanings:

$R^1$ and $R^2$ independently of one another are a radical from the group 1.01–1.66 (Table 1) or $R^1$ and $R^2$ are together a radical from the group 2.01–2.04 (Table 2), $R^3$ is a radical from the group 3.01–3.11 (Table 3), $R^4$ is a radical from the group 4.01–4.05 (Table 4), $R^5$ is a radical from the group 5.01–5.08 (Table 5), $R^5$ and $R^6$ together are a radical from the group 56.01–56.31 (Table 6), $R^6$ is a radical from the group 6.01–6.07 (Table 7), where A is a radical from the group A.01–A.33 (Table 8), B is a radical from the group B.01–B.138 (Table 9), $R^{10}$ is a radical from the group 10.01–10.22 (Table 10), $R^{11}$ is a radical from the group 11.01–11.154 (Table 11), $R^{12}$ and $R^{13}$ independently of one another are a radical from the group 12.01–12.17 (Table 12), $X^1$ and $X^2$ independently of one another are oxygen or sulfur, $R^{17}$ and $R^{18}$ independently of one another are a radical from the group 17.01–17.12 (Table 13) or $R^{17}$ and $R^{18}$ together are a radical from the group 18.01–18.61 (Table 14), where the substituents $R^1$, $R^2$, $R^3$, $R^4$, $R^5$ and $R^6$ can be combined with one another in any desired manner, with the proviso that either $R^5$ and $R^6$ together cannot form any of the radicals 56.01–56.06 if $R^1$ and $R^2$ are hydrogen and $R^4$ is simultaneously fluorine, or $R^5$ and $R^6$ together cannot form a radical 56.22 or 56.23 if $R^1$ and $R^2$ are hydrogen.

TABLE 1

| No. | $R^1, R^2$ |
|---|---|
| 1.01 | H |
| 1.02 | $CH_3$ |
| 1.03 | $C_2H_5$ |
| 1.04 | n-$C_3H_7$ |
| 1.05 | $CH(CH_3)_2$ |
| 1.06 | n-$C_4H_9$ |
| 1.07 | i-$C_4H_9$ |
| 1.08 | s-$C_4H_9$ |
| 1.09 | $C(CH_3)_3$ |
| 1.10 | n-$C_5H_{11}$ |
| 1.11 | n-$C_6H_{13}$ |
| 1.12 | $CH_2$—CH=$CH_2$ |
| 1.13 | $CH_2$—CH=$CHCH_3$ |
| 1.14 | $CH_2$—C≡CH |
| 1.15 | $CH_2C$≡C—$SiCH_3$ |
| 1.16 | $CH_2OCH_3$ |
| 1.17 | $(CH_2)_3$—$OCH_3$ |
| 1.18 | $(CH_2)_3$—$OC_2H_5$ |
| 1.19 | CN |
| 1.20 | $(CH)_2$—CN |
| 1.21 | $COOCH_3$ |
| 1.22 | $COOC_2H_5$ |
| 1.23 | COO(n-$C_3H_7$) |
| 1.24 | COO—$CH(CH_3)_2$ |
| 1.25 | COO(n-$C_4H_9$) |
| 1.26 | COO(i-$C_4H_9$) |
| 1.27 | COO(s-$C_4H_9$) |
| 1.28 | COO—$C(CH_3)_3$ |
| 1.29 | CHO |
| 1.30 | $COCH_3$ |
| 1.31 | $COC_2H_5$ |
| 1.32 | CO—$CH(CH_3)_2$ |
| 1.33 | CO-phenyl |
| 1.34 | CO-(4-Cl-phenyl) |
| 1.35 | CO-(4F-phenyl) |
| 1.36 | CO-(2,4-$Cl_2$-phenyl) |
| 1.37 | $CH_2$—$COOCH_3$ |
| 1.38 | $(CH_2)_2$—$COOCH_3$ |
| 1.39 | $(CH_2)_4$—$COOC_2H_5$ |
| 1.40 | CH=CH—$COOCH_3$ |
| 1.41 | CH=CH—$COOC_2H_5$ |
| 1.42 | Cyclopropyl |
| 1.43 | Cyclobutyl |
| 1.44 | Cyclopentyl |
| 1.45 | Cyclohexyl |
| 1.46 | Cycloheptyl |
| 1.47 | Cyclooctyl |
| 1.48 | $(CH_2)_3$—Cl |
| 1.49 | $(CH_2)_3$—F |
| 1.50 | Phenyl |
| 1.51 | 4-Cl-phenyl |
| 1.52 | 4-F-phenyl |
| 1.53 | 3-F-phenyl |
| 1.54 | 2-F-phenyl |
| 1.55 | 2-Cl-phenyl |

TABLE 1-continued

| No. | $R^1, R^2$ |
|---|---|
| 1.56 | 3-Cl-phenyl |
| 1.57 | 4-$CH_3$-phenyl |
| 1.58 | 4-Br-phenyl |
| 1.59 | 4-$OCH_3$-phenyl |
| 1.60 | 4-$NO_2$-phenyl |
| 1.61 | 3-$CF_3$-phenyl |
| 1.62 | 4-$CF_3$-phenyl |
| 1.63 | 2-$CF_3$-phenyl |
| 1.64 | 2,4-$Cl_2$-phenyl |
| 1.65 | 3,4-$Cl_2$-phenyl |
| 1.66 | 2-Cl,4-F-phenyl |

TABLE 2

| No. | $R^1, R^2$ |
|---|---|
| 2.01 | —$(CH_2)_2$— |
| 2.02 | —$(CH_2)_4$— |
| 2.03 | —$(CH_2)_5$— |
| 2.04 | —$(CH_2)_6$— |

TABLE 3

| No. | $R^3$ |
|---|---|
| 3.01 | H |
| 3.02 | $CH_3$ |
| 3.03 | $C_2H_5$ |
| 3.04 | n-$C_3H_7$ |
| 3.05 | i-$C_3H_7$ |
| 3.06 | n-$C_4H_9$ |
| 3.07 | i-$C_4H_9$ |
| 3.08 | s-$C_4H_9$ |
| 3.09 | $C(CH_3)_3$ |
| 3.10 | n-$C_5H_{11}$ |
| 3.11 | n-$C_6H_{13}$ |

TABLE 4

| No. | $R^4$ |
|---|---|
| 4.01 | H |
| 4.02 | F |
| 4.03 | Cl |
| 4.04 | Br |
| 4.05 | I |

TABLE 5

| No. | $R^5$ |
|---|---|
| 5.01 | F |
| 5.02 | Cl |
| 5.03 | Br |
| 5.04 | I |
| 5.05 | CN |
| 5.06 | $NO_2$ |
| 5.07 | $CF_3$ |
| 5.08 | H |

TABLE 6

| No. | $R^5, R^6$ |
|---|---|
| 56.01 | —O—$CH_2$—CO—N($CH_3$)— |
| 56.02 | —O—$CH_2$—CO—NH— |
| 56.03 | —O—$CH_2$CO—N($CH_2C$≡CH)— |

TABLE 6-continued

| No. | R⁵, R⁶ |
|---|---|
| 56.04 | —OCH(CH₃)—CO—N(CH₂C≡CH) |
| 56.05 | —O—CH(CH₃)—CO—N(i-C₃H₇)— |
| 56.06 | —O—CH₂—CO—N(i-C₃H₇)— |
| 56.07 | —S—CH₂—CO—N(CH₂C≡CH)— |
| 56.08 | —CH₂—CH₂—CO—N(CH₂C≡CH)— |
| 56.09 | —O—CO—N(CH₃)— |
| 56.10 | —O—CO—N(CH₂C≡CH)— |
| 56.11 | —S—CO—N(CH₃)— |
| 56.12 | —S—CO—N(CH₂C≡CH)— |
| 56.13 | —N=CH—CO—N(CH₂C≡CH)— |
| 56.14 | —N=CH—CO—N(CH₃)— |
| 56.15 | —N=CH—CO—N(i-C₃H₇)— |
| 56.16 | —O—(CH₂)₂—C(=N—OCH₃)— |
| 56.17 | —O—(CH₂)₂—C(=N—OC₂H₅)— |
| 56.18 | —O—CO—CH₂—N(CH₂C≡CH)— |
| 56.19 | —O—CO—CH(CH₃)—N—(CH₂C≡CH)— |
| 56.20 | —O—CO—CH₂—N(i-C₃H₇)— |
| 56.21 | —O—CO—CH(CH₃—N(i-C₃H₇)— |
| 56.22 | —CH=CH—N—(CH₂C≡CH)— |
| 56.23 | —CH=CH—N(iC₃H₇)— |
| 56.24 | —CH=CH—N(CH₂C≡CH)— |
| 56.25 | —C(CH₃)=CH—N(CH₂C≡CH)— |
| 56.26 | —S—C(O-iC₃H₇)=N— |
| 56.27 | —S—C(OCH₂C≡CH)=N— |
| 56.28 | —O—CH₂—CH(CH₃)—N(CH₂C≡CH)— |
| 56.29 | —O—CH₂—CH(CH₃)—N(CH₂C≡CH)— |
| 56.30 | —O—CH₂—CH(CF₃)—N(CH₂C≡CH)— |
| 56.31 | —S—CH₂—CO—N(CH₃)— |

TABLE 7

| No. | R⁶ |
|---|---|
| 6.01 | A-CO—B |
| 6.02 | C(R¹⁰)=O |
| 6.03 | C(R¹⁰)=S |
| 6.04 | C(R¹⁰)=N(R¹¹) |
| 6.05 | C(X¹R¹⁷)(X²R¹⁸)R¹⁰ |
| 6.06 | P(R¹²)(R¹³)=O |
| 6.07 | CHR¹⁰—CHR¹¹—CO—B |

TABLE 8

| No. | A |
|---|---|
| A.01 | —CH=CH— |
| A.02 | —CH=CH—CH₂— |
| A.03 | —CH=CCl— |
| A.04 | —CH=CBr— |
| A.05 | —CH=CI— |
| A.06 | —CH=C(CH₃)— |
| A.07 | —CH=C(C₂H₅)— |
| A.08 | —CH=C(CN)— |
| A.09 | —CH=C(COOCH₃)— |
| A.10 | —CH=C(COOC₂H₅)— |
| A.11 | —CH=C(OCOCH₃)— |
| A.12 | —CH=C(COCH₃)— |
| A.13 | —C≡C— |
| A.14 | —C≡C—CH₂— |
| A.15 | —C≡C—CH₂—CH₂— |
| A.16 | —C≡C—CH(CH₃)— |
| A.17 | —C(CH₃)=CH— |
| A.18 | —C(CH₃)=CCl— |
| A.19 | —C(CH₃)=CBr— |
| A.20 | —C(CH₃)=C(CH₃)— |
| A.21 | —C(CH₃)=C(CN)— |
| A.22 | —CH=CF— |
| A.23 | —CH₂— |
| A.24 | —CH₂—CH₂ |
| A.25 | —CH₂CH(CN)— |
| A.26 | —CH₂—CHCl— |
| A.27 | —CH₂—CHBr— |
| A.28 | —CH₂—CHF— |
| A.29 | —CH₂—CH(CH₃)— |

TABLE 8-continued

| No. | A |
|---|---|
| A.30 | —CH₂CH(COOCH₃)— |
| A.31 | —CH₂—CH(COCH₃)— |
| A.32 | —(CH₂)₃— |
| A.33 | —(CH₂)₄— |

TABLE 9

| No. | B |
|---|---|
| B.01 | H |
| B.02 | OH |
| B.03 | OCH₃ |
| B.04 | OC₂H₅ |
| B.05 | O-n-C₃H₇ |
| B.06 | O-i-C₃H₇ |
| B.07 | O-n-C₃H₉ |
| B.08 | O-i-C₄H₉ |
| B.09 | O-s-C₄H₉ |
| B.10 | O-tert.-C₄H₉ |
| B.11 | O-n-C₅H₁₁ |
| B.12 | O-n-C₆H₁₃ |
| B.13 | O—CH₂CH=CH₂ |
| B.14 | O—CH(CH₃)CH=CH₂ |
| B.15 | O—CH—CH=CH—CH₂ |
| B.16 | O—CH₂—C≡CH |
| B.17 | O—CH(CH₃)—C≡CH |
| B.18 | O—CH₂—C≡C—CH₃ |
| B.19 | O-cyclopropyl |
| B.20 | O-cyclobutyl |
| B.21 | O-cyclopentyl |
| B.22 | O-cyclohexyl |
| B.23 | O—CH₂—CF₃ |
| B.24 | O—CH₂CCl₃ |
| B.25 | O—(CH₂)₃—Br |
| B.26 | O-phenyl |
| B.27 | O-(2-F-phenyl) |
| B.28 | O-(2-Cl-phenyl) |
| B.29 | O-(2-Br-phenyl) |
| B.30 | O-(3-F-phenyl) |
| B.31 | O-(3-Cl-phenyl) |
| B.32 | O-(3-Br-phenyl) |
| B.33 | O-(4-F-phenyl) |
| B.34 | O-(4-Cl-phenyl) |
| B.35 | O-(4-Br-phenyl) |
| B.36 | O-(4-OCH₃-phenyl) |
| B.37 | O-(4-CN-phenyl) |
| B.38 | O-(4-COOCH₃-phenyl) |
| B.39 | O-(CH₃-phenyl) |
| B.40 | O-(2,4-Cl₂-phenyl) |
| B.41 | O-(2,4-(CH₃)₂-phenyl) |
| B.42 | O-CH₂CN |
| B.43 | O-CH₂CH=CCl₂ |
| B.44 | O-CH₂CH=CHCl |
| B.45 | O-CH₂OCH₃ |
| B.46 | O—CH₂OC₂H₅ |
| B.47 | O—C₂H₄OCH₃ |
| B.48 | O—C₂H₄OC₂H₅ |
| B.49 | O—CH(CH₃)—OCH₃ |
| B.50 | O—CH(CH₃)—OC₂H₅ |
| B.51 | OCH₂C=NOCH₃ |
| B.52 | O—C₂H₅C=NOCH₃ |
| B.53 | O—CH₂C=NOC₂H₅ |
| B.54 | O—C(O)CH₃ |
| B.55 | O—C(O)C₂H₅ |
| B.56 | O—C₂H₄C=NOC₂H₅ |
| B.57 | SCH₃ |
| B.58 | SC₂H₅ |
| B.59 | S-n-C₃H₇ |
| B.60 | S-i-C₃H₇ |
| B.61 | S—CH₂CH=CH₂ |
| B.62 | S—CH₂C≡CH |
| B.63 | S-phenyl |
| B.64 | S-CH₂CN |
| B.65 | S—CH₂OCH₃ |
| B.66 | CH₃ |

TABLE 9-continued

| No. | B |
|---|---|
| B.67 | $C_2H_7$ |
| B.68 | $n\text{-}C_3H_7$ |
| B.69 | $i\text{-}C_3H_7$ |
| B.70 | $n\text{-}C_4H_9$ |
| B.71 | $i\text{-}C_4H_9$ |
| B.72 | $s\text{-}C_4H_9$ |
| B.73 | $tert.\text{-}C_4H_9$ |
| B.74 | $n\text{-}C_5H_{11}$ |
| B.75 | $n\text{-}C_6H_{13}$ |
| B.76 | $CH_2CH{=}CH_2$ |
| B.77 | $CH_2C{\equiv}CH$ |
| B.78 | $CH(CH_3)CH{=}CH_2$ |
| B.79 | $CH(CH_3)C{\equiv}CH$ |
| B.80 | $CH_2Cl$ |
| B.81 | $CH_2Br$ |
| B.82 | $CHCl_2$ |
| B.83 | $CF_3$ |
| B.84 | Cyclopropyl |
| B.85 | Cyclobutyl |
| B.86 | Cyclopentyl |
| B.87 | CyclohexyL |
| B.88 | Phenyl |
| B.89 | 2-F-phenyl |
| B.90 | 3-F-phenyl |
| B.91 | 4-F-phenyl |
| B.92 | 2-Cl-phenyl |
| B.93 | 4-Cl-phenyl |
| B.94 | $2,4\text{-}Cl_2$-phenyl |
| B.95 | $CH_2{-}OCH_3$ |
| B.96 | $CH(OCH_3)_2$ |
| B.97 | $CH_2{-}SCH_3$ |
| B.98 | $NH_2$ |
| B.99 | $NHCH_3$ |
| B.100 | $NH\text{-}n\text{-}C_3H_7$ |
| B.101 | $NH\text{-}i\text{-}C_3H_7$ |
| B.102 | $NH\text{-}n\text{-}C_4H_9$ |
| B.103 | $N(CH_3)_2$ |
| B.104 | $N(C_2H_5)_2$ |
| B.105 | $N(CH_3)C_2H_5$ |
| B.106 | $N(n\text{-}C_3H_7)_2$ |
| B.107 | $NH{-}CH_2CH{=}CH_2$ |
| B.108 | $NH{-}CH(CH_3){-}CH{=}CH_2$ |
| B.109 | $NH{-}CH_2{-}C{\equiv}CH$ |
| B.110 | $NH{-}CH(CH_3){-}C{\equiv}CH$ |
| B.111 | $N(CH_3){-}CH_2CH{=}CH$ |
| B.112 | $N(CH_3){-}CH_2C{\equiv}CH$ |
| B.113 | NH-cyclopropyl |
| B.114 | NH-cyclobutyl |
| B.115 | NH-cyclopentyl |
| B.116 | NH-cyclohexyl |
| B.117 | $N(CH_3)$-cyclohexyl |
| B.118 | $N(C_2H_5)$-cyclohexyl |
| B.119 | $NH\text{-}COCH_3$ |
| B.120 | $NH{-}COC_2H_5$ |
| B.121 | $NH{-}COOCH_3$ |
| B.122 | $NH{-}CH_2OCH_3$ |
| B.123 | $NH{-}(CH_2)_2CCH_3$ |
| B.124 | N-piperidinyl |
| B.125 | N-pyrrolidinyl |
| B.126 | N-morpholino |
| B.127 | N-piperazinyl |
| B.128 | NH-phenyl |
| B.129 | $NH\text{-}(2\text{-}CH_3\text{-phenyl})$ |
| B.130 | NH-(2-F-phenyl) |
| B.131 | NH-(4-F-phenyl) |
| B.132 | NH-(2-Cl-phenyl) |
| B.133 | NH-(4-Cl-phenyl) |
| B.134 | $NH\text{-}(2,4\text{-}Cl_2\text{-phenyl})$ |
| B.135 | $O{-}CO{-}OCH_3$ |
| B.136 | $O{-}CO{-}OC_2H_5$ |
| B.137 | $O{-}CH_2{-}COOCH_3$ |
| B.138 | $O{-}CH(CH_3){-}COOCH_3$ |

TABLE 10

| No. | $R^{10}$ |
|---|---|
| 10.01 | H |
| 10.02 | $CH_3$ |
| 10.03 | $C_2H_5$ |
| 10.04 | $n\text{-}C_3H_7$ |
| 10.05 | $i\text{-}C_3H_7$ |
| 10.06 | $n\text{-}C_4H_9$ |
| 10.07 | $i\text{-}C_4H_9$ |
| 10.08 | $s\text{-}C_4H_9$ |
| 10.09 | $tert.\text{-}C_4H_9$ |
| 10.10 | $n\text{-}C_5H_{11}$ |
| 10.11 | $n\text{-}C_6H_{13}$ |
| 10.12 | $CH_2{-}CH{=}CH_2$ |
| 10.13 | $CH_2{-}C{\equiv}CH$ |
| 10.14 | $CF_3$ |
| 10.15 | $CCl_3$ |
| 10.16 | Cyclopropyl |
| 10.17 | Cyclobutyl |
| 10.18 | Cyclopentyl |
| 10.19 | Cyclohexyl |
| 10.20 | CN |
| 10.21 | $CO{-}OCH_3$ |
| 10.22 | $CO{-}OC_2H_5$ |

TABLE 11

| No. | $R^{11}$ |
|---|---|
| 11.001 | H |
| 11.002 | $CH_3$ |
| 11.003 | $C_2H_5$ |
| 11.004 | $n\text{-}C_3H_7$ |
| 11.005 | $CH(CH_3)_2$ |
| 11.006 | $n\text{-}C_4H_9$ |
| 11.007 | $n\text{-}C_5H_{11}$ |
| 11.008 | $n\text{-}C_6H_{13}$ |
| 11.009 | $CH_2CH{=}CH_2$ |
| 11.010 | $CH(CH_3){-}CH{=}CH_2$ |
| 11.011 | $CH_2{-}CH{=}CH{-}CH_2$ |
| 11.012 | $CH_2{-}C{\equiv}CH$ |
| 11.013 | $CH(CH_3){-}C{\equiv}CH$ |
| 11.014 | $CH_2{-}C{\equiv}C{-}CH_3$ |
| 11.015 | Cyclopropyl |
| 11.016 | Cyclobutyl |
| 11.017 | Cyclopentyl |
| 11.018 | Cyclohexyl |
| 11.019 | Cycloheptyl |
| 11.020 | $(CH_2)_2Cl$ |
| 11.021 | $CH_2Cl$ |
| 11.022 | Phenyl |
| 11.023 | 2-F-phenyl |
| 11.024 | 3-F-phenyl |
| 11.025 | 4-F-phenyl |
| 11.026 | 2-Cl-phenyl |
| 11.027 | 3-Cl-phenyl |
| 11.028 | 4-Cl-phenyl |
| 11.029 | 2-Br-phenyl |
| 11.030 | 3-Br-phenyl |
| 11.031 | 4-Br-phenyl |
| 11.032 | $2\text{-}CH_3$-phenyl |
| 11.033 | $3\text{-}CH_3$-phenyl |
| 11.034 | $4\text{-}CH_3$-phenyl |
| 11.035 | $2\text{-}CF_3$-phenyl |
| 11.036 | $3\text{-}CF_3$-phenyl |
| 11.037 | $4\text{-}CF_3$-phenyl |
| 11.038 | $2\text{-}OCH_3$-phenyl |
| 11.039 | $3\text{-}OCH_3$-phenyl |
| 11.040 | $4\text{-}OCH_3$-phenyl |
| 11.041 | $4\text{-}NO_2$-phenyl |
| 11.042 | 4-CN-phenyl |
| 11.043 | $2,4\text{-}Cl_2$-phenyl |
| 11.044 | $2,4\text{-}(CH_3)_2$-phenyl |
| 11.045 | $CH_2{-}OCH_3$ |
| 11.046 | $(CH_2)_2{-}OC_2H_5$ |
| 11.047 | OH |
| 11.048 | $OCH_2COOCH_3$ |

TABLE 11-continued

| No. | $R^{11}$ |
|---|---|
| 11.049 | $OCH_2COOC_2H_5$ |
| 11.050 | $OCH_2COO—CH(CH_3)_2$ |
| 11.051 | $OCH_2COO—C(CH_3)_3$ |
| 11.052 | $O—CH_2CH=CH_2$ |
| 11.053 | $O—CH(CH_3)CH=CH_2$ |
| 11.054 | $O—CH_2C\equiv CH$ |
| 11.055 | $O—CH(CH_3)—C\equiv CH$ |
| 11.056 | $O—CH_2—C\equiv C—CH_3$ |
| 11.057 | $O—CH_2—CH=CH—CH_3$ |
| 11.058 | O-cyclopentyl |
| 11.059 | O-cyclohexyl |
| 11.060 | O-cyclopent-3-enyl |
| 11.061 | O-cyclohex-3-enyl |
| 11.062 | $O—(CH_2)_2—Cl$ |
| 11.063 | $O—(CH_2)_2—Cl$ |
| 11.064 | $O—(CH_2)—F$ |
| 11.065 | $O—CH_2—CF_3$ |
| 11.066 | $O—(CH_2)_2—Br$ |
| 11.067 | $O—CH_2—CH=CHCl$ |
| 11.068 | $O—CH_2—C(Cl)=CH_2$ |
| 11.069 | $O—CH_2—C(Br)=CH_2$ |
| 11.070 | $O—CH_2—CH=C(Cl)—CH_3$ |
| 11.071 | $O—CH_2—C(Cl)=CCl_2$ |
| 11.072 | $O—CH_2$-cyclopropyl |
| 11.073 | $O—CH_2$-cyclobutyl |
| 11.074 | $O—CH_2$-cyclopentyl |
| 11.075 | $O—CH_2$-cyclohexyl |
| 11.076 | $O—CH_2$-cycloheptyl |
| 11.077 | $O—CO—CH_3$ |
| 11.078 | $O—CO—C_2H_5$ |
| 11.079 | $O—CH_2—CN$ |
| 11.080 | $O—(CH_2)_3—CN$ |
| 11.081 | $O—CH_2—OCH_3$ |
| 11.082 | $O—CH_2—OC_2H_5$ |
| 11.083 | $O—(CH_2)_2—OCH_3$ |
| 11.084 | $O—(CH_2)_2—OC_2H_5$ |
| 11.085 | $O—(CH_2)_3—OC_2H_5$ |
| 11.086 | $O—(CH_2)_2—CO—OCH_3$ |
| 11.087 | $O—(CH_2)_2—CO—OC_2H_5$ |
| 11.088 | $O—C(CH_3)—CO—OCH_3$ |
| 11.089 | $O—C(CH_3)—CO—OC_2H_5$ |
| 11.090 | $O—(CH_2)_2—OH$ |
| 11.091 | $O—CH_2—SCH_3$ |
| 11.092 | $O—(CH_2)_2—N(CH_3)_2$ |
| 11.093 | $O—(CH_2)_2—N(C_2H_5)_2$ |
| 11.094 | $O—CH_2$-phenyl |
| 11.095 | $O—(CH_2)_2$-phenyl |
| 11.096 | $O—(CH_2)_3$-phenyl |
| 11.097 | $O—(CH_2)_4$-phenyl |
| 11.098 | $O—(CH_2)_4$-(4-Cl-phenyl) |
| 11.099 | $O—(CH_2)_4$-(4-$CH_3$-phenyl) |
| 11.100 | $O—(CH_2)_4$-(4-$CH_3$-phenyl) |
| 11.101 | $O—(CH_2)_4$-(4-F-phenyl) |
| 11.102 | $O—CH_2CH=CH$-phenyl |
| 11.103 | $O—CH_2CH=CH$-(4-F-phenyl) |
| 11.104 | $O—CH_2CH=CH$-(4-Cl-phenyl) |
| 11.105 | $O—CH_2CH=CH$-(3-$OCH_3$-phenyl) |
| 11.106 | $O—(CH_2)_2—CH=CH$-(4-F-phenyl) |
| 11.107 | $O—(CH_2)_2—CH=CH$-(4-Cl-phenyl) |
| 11.108 | $O—(CH_2)—CH=CH$-(3,4-$Cl_2$-phenyl) |
| 11.109 | $O—CH_2—CH=C(CH_3)$-(4-F-phenyl) |
| 11.110 | $O—CH_2—C\equiv C—CH_2$-phenyl |
| 11.111 | $O—(CH_2)_2—O$-phenyl |
| 11.112 | $O—(CH_2)_2—OCH_2$-phenyl |
| 11.113 | $O—(CH_2)_2—OCH_2$-(4-F-phenyl) |
| 11.114 | $O—CH_2CH=CH—CH_2—O$-phenyl |
| 11.115 | $O—CH_2—C\equiv C—CH_2—O$-phenyl |
| 11.116 | $O—CH_2—C\equiv C—CH_2—O$-(4-F-phenyl) |
| 11.117 | $O—(CH_2)_2—SCH_2$-phenyl |
| 11.118 | $O—(CH_2)_2—SCH_2$-(4-Cl-phenyl) |
| 11.119 | $O—(CH_2)_2—N(CH_3)—CH_2$-phenyl |
| 11.120 | $NH_2$ |
| 11.121 | $NH—CH_3$ |
| 11.122 | $NH—C_2H_5$ |
| 11.123 | $NH$-n-$C_3H_7$ |
| 11.124 | $NH$-i-$C_3H_7$ |
| 11.125 | $NH$-n-$C_4H_9$ |
| 11.126 | $NH$-i-$C_4H_9$ |
| 11.127 | $NH$-s-$C_4H_9$ |
| 11.128 | $NH—C(CH_3)_3$ |
| 11.129 | NH-cyclopropyl |
| 11.130 | NH-cyclobutyl |
| 11.131 | NH-cyclopentyl |
| 11.132 | NH-cyclohexyl |
| 11.133 | NH-cyclohepty |
| 11.134 | $N(CH_3)_2$ |
| 11.135 | $N(C_2H_5)_2$ |
| 11.136 | $NH—CH_2CH=CH_2$ |
| 11.137 | $NH—CH_2C\equiv CH$ |
| 11.138 | $NH—CH_2—CF_3$ |
| 11.139 | $NH—CO—CH_3$ |
| 11.140 | $NH—COC_2H_5$ |
| 11.141 | $NH—CO—OCH_3$ |
| 11.142 | $NH—CO—OC_2H_5$ |
| 11.143 | $NH—COO—C(CH_3)_3$ |
| 11.144 | N-pyrrolidinyl |
| 11.145 | N-piperidinyl |
| 11.146 | N-morpholino |
| 11.147 | N-piperazinyl |
| 11.148 | NH-phenyl |
| 11.149 | NH-(4-Cl-phenyl) |
| 11.150 | NH-(4-F-phenyl) |
| 11.151 | NH-(4-$OCH_3$-phenyl) |
| 11.152 | NH-(2,4-$Cl_2$-phenyl) |
| 11.153 | $CH_2—OCH_3$ |
| 11.154 | $(CH_2)_2—OCH_3$ |

TABLE 12

| No. | $R^{12}$, $R^{13}$ |
|---|---|
| 12.01 | $OCH_3$ |
| 12.02 | $OC_2H_5$ |
| 12.03 | $O—CH(CH_3)_2$ |
| 12.04 | $O$-n$C_3H_7$ |
| 12.05 | $O$-n$C_4H_9$ |
| 12.06 | $O$-i$C_4H_9$ |
| 12.07 | $O$-s$C_4H_9$ |
| 12.08 | $O—C(CH_3)_3$ |
| 12.09 | Phenyl |
| 12.10 | 2-Cl-phenyl |
| 12.11 | 3-Cl-phenyl |
| 12.12 | 2-F-phenyl |
| 12.13 | 3-F-phenyl |
| 12.14 | 4-F-phenyl |
| 12.15 | 4-$NO_2$-phenyl |
| 12.16 | 2,4-$Cl_2$-phenyl |
| 12.17 | 2-F,4-CN-phenyl |

TABLE 13

| No. | $R^{17}$, $R^{18}$ |
|---|---|
| 17.01 | $CH_3$ |
| 17.02 | $C_2H_5$ |
| 17.03 | n-$C_3H_7$ |
| 17.04 | i-$C_3H_7$ |
| 17.05 | n-$C_4H_9$ |
| 17.06 | i-$C_4H_9$ |
| 17.07 | s-$C_4H_9$ |
| 17.08 | $C(CH_3)_3$ |

TABLE 13-continued

| No. | $R^{17}, R^{18}$ |
|---|---|
| 17.09 | n-$C_5H_{11}$ |
| 17.10 | n-$C_6H_{13}$ |
| 17.11 | $CH_2CH=CH_2$ |
| 17.12 | $CH(CH_3)-CH=CH_2$ |

TABLE 14

| No. | $R^{17}$ and $R^{18}$ together |
|---|---|
| 18.01 | —$(CH_2)_2$— |
| 18.02 | —$CH(CH_3)$—$CH_2$— |
| 18.03 | —$CH(C_2H_5)$—$CH_2$— |
| 18.04 | —$CH(CH_3)$—$CH$—$(CH_3)$— |
| 18.05 | —$C(CH_3)_2$—$CH_2$— |
| 18.06 | —$CH(CH=CH_2)$—$CH_2$— |
| 18.07 | —$CH(CH_2Cl)$—$CH_2$— |
| 18.08 | —$CH(CH_2Br)$—$CH_2$— |
| 18.09 | —$CH(CH_2OH)$—$CH_2$— |
| 18.10 | —$CH(CH_2OCH_3)$—$CH_2$— |
| 18.11 | —$CH(CH_2OC_2H_5)$—$CH_2$— |
| 18.12 | —$CH(CH_2OCH_2CH=CH_2)$—$CH_2$— |
| 18.13 | —$CH(CH_2OCH_2C≡CH)$—$CH_2$— |
| 18.14 | —$CH(COOH)$—$CH_2$— |
| 18.15 | —$CH(COOCH_3)$—$CH_2$— |
| 18.16 | —$CH(COOC_2H_5)$—$CH_2$— |
| 18.17 | —$CH(COO$-n-$C_3H_7)$—$CH_2$— |
| 18.18 | —$CH(COO$—$CH(CH_3)_2)$—$CH_2$— |
| 18.19 | —$CH(COO$-n-$C_4H_9)$—$CH_2$— |
| 18.20 | —$CH(COO$-n-$C_5H_{11})$—$CH_2$— |
| 18.21 | —$CH(COO$-n-$C_6H_{13})$—$CH_2$— |
| 18.22 | —$(CH_2)_3$— |
| 18.23 | —$CH(CH_3)$—$(CH_2)_2$— |
| 18.24 | —$CH_2$—$CH(CH_3)$—$CH_2$— |
| 18.25 | —$CH(C_2H_5)$—$(CH_2)_2$— |
| 18.26 | —$CH_2$—$CH(C_2H_5)$—$CH_2$— |
| 18.27 | —$CH(CH_3)$—$CH_2$—$CH(CH_3)$— |
| 18.28 | —$CH_2$—$C(CH_3)_2$—$CH_2$— |
| 18.29 | —$CH(CH_2OH)$—$(CH_2)_2$— |
| 18.30 | —$CH_2$—$CH(CH_2OH)$—$CH_2$— |
| 18.31 | —$CH(CH_2OCH_3)$—$(CH_2)_2$— |
| 18.32 | —$CH(CH_2OCH_2CH=CH_2)$—$(CH_2)_2$— |
| 18.33 | —$CH(CH_2O$—$CO$—$CH_3)$—$CH_2$— |
| 18.34 | —$CH(CH_2OCH_2C≡CH)$—$(CH_2)_2$— |
| 18.35 | —$CH(CH_2OC(O)CH_3)$—$(CH_2)_2$— |
| 18.36 | —$CH_2$—$CH(CH_2OCH_3)$—$CH_2$— |
| 18.37 | —$CH_2$—$CH(CH_2OCH_2CH=CH_2)$—$CH_2$— |
| 18.38 | —$CH_2$—$CH(CH_2OCH_2C≡CH)$—$CH_2$— |
| 18.39 | —$CH_2$—$CH(CH_2OC(O)CH_3)$—$CH_2$— |
| 18.40 | —$CH(CH_2Cl)$—$(CH_2)_2$ |
| 18.41 | —$CH_2$—$CH(CH_2Cl)$—$CH_2$— |
| 18.42 | —$C(CH_3)$—$(COOCH_3)$—$CH_2$— |
| 18.43 | —$C(CH_3)$—$(COOC_2H_5)$—$CH_2$— |
| 18.44 | —$C(CH_3)(COO$-n-$C_3H_7)$—$CH_2$— |
| 18.45 | —$C(CH_3)(COO$-n-$C_4H_6)$—$CH_2$— |
| 18.46 | —$CH(CH_2CN)$—$CH_2$— |
| 18.47 | —$CH(CH_2CN)$—$(CH_2)_2$— |
| 18.48 | —$CH_2$—$CH(CH_2CN)$—$CH_2$— |
| 18.49 | —$CH_2$—$O$—$CH_2$— |
| 18.50 | —$CH_2$—$NH$—$CH_2$— |
| 18.51 | —$CH_2$—$N(CH_3)$—$CH_2$— |
| 18.52 | —$(CH_2)_4$— |
| 18.53 | —$CH_2$—$CH=CH$—$CH_2$— |
| 18.54 | —$CH_2$—$O$—$(CH_2)_2$— |
| 18.55 | —$CO$—$CH_2$— |
| 18.56 | —$CO$—$(CH_2)_2$— |
| 18.57 | —$CH_2$—$CO$—$CH_2$— |
| 18.58 | —$CO$—$C(CH_3)_2$— |
| 18.59 | —$CO$—$O$—$CH_2$— |
| 18.60 | —$CH_2$—$S$—$CH_2$ |
| 18.61 | —$CH(CH_2O$—$CO$—$CH_3)$—$CH_2$— |

The substituted isoindolones I are obtainable in various ways, in fact preferably by one of the following processes:

a) dehydration of an isoindolone of the formula II with an acidic compound and/or with a dehydrating agent:

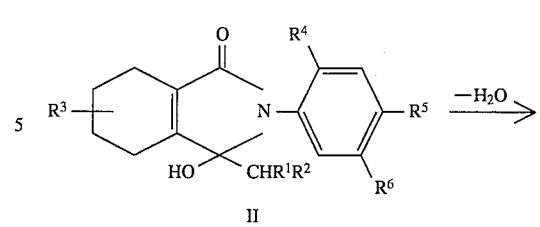

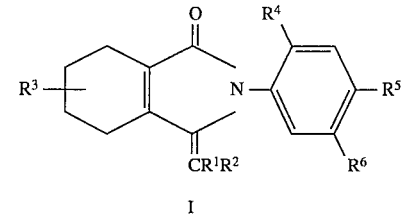

The dehydration is carried out in an inert organic solvent, suitable solvents for this purpose being, for example, aliphatic hydrocarbons such as n-hexane, aromatic hydrocarbons such as toluene such as toluene and o-, m- or p-xylene, chlorinated hydrocarbons such as dichloromethane and chlorobenzene, ethers such as diethyl ether, tetrahydrofuran, dioxane and diglyme, amides such as dimethylformamide and N-methylpyrrolidone or sulfoxides such as dimethyl sulfoxide.

The reaction is particularly preferably carried out in a solvent which forms an azeotrope with water, in particular in toluene or dichloromethane, and the resulting water of reaction is continuously removed from the reaction mixture, for example by means of a Dean-Stark apparatus.

Suitable acidic catalysts are, for example, inorganic protic acids, in particular sulfuric acid and hydrohalic acids such as hydrochloric acid, sulfonic acids such as p-toluenesulfonic acid, or acidic inorganic salts such as potassium hydrogen sulfate.

Suitable dehydrating agents are, for example, molecular sieves and phosphorus pentoxide.

The reaction temperature is customarily from 0° to 150° C., preferably from 20° C. to the boiling point of the reaction mixture.

Since the reaction is not recognizably dependent on the pressure, the reaction is expediently carried out at atmospheric pressure or under the autogenous pressure of the respective solvent.

The compounds of the formula II are also novel. As a rule, they can be prepared from tetrahydrophthalimides III under the action of a suitable organometallic compound IV, Grignard reagents being particularly suitable:

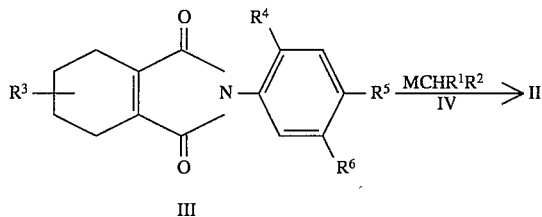

M is a metal atom which can be halogenated, in particular halogenated magnesium, particularly preferably magnesium iodide.

The reaction is carried out under the reaction conditions customary for the Grignard reaction (cf., for example, U.S. Pat. No. 3,992,189, Houben-Weyl, Methoden d. Organischen Chemie (Methods of Organic Chemistry), Vol. 13/2a, Georg Thieme Verlag, Stuttgart 1973, p. 53 et seq. and R. C. Larock, Comprehensive Organic Transformations, Verlag Chemie, Weinheim 1989, p. 553 et seq. and the references cited therein).

When using metals other than magnesium, for example lithium, it may be advantageous to work in the presence of a Lewis acid, a complexing agent or an additional base.

Suitable Lewis acids are, in particular, titanium tetrachloride or boron trifluoride etherate.

Suitable complexing agents are, for example, crown ethers such as [18]crown-6, amides such as tetramethylethylenediamine, ureas such as 1,3-dimethyl-3,4,5,6-tetrahydro-2(1H)-pyrimidinone or hexamethylphosphoramide (cf., for example, Houben-Weyl, Methoden der Organischen Chemie (Methods of Organic Chemistry), Vol. E14a/2, Stuttgart 1991, p. 426 et seq.; A. I. Meyers and B. A. Lefkin, Tetrahedron Lett. (1987), 28, 1745; M. Yamaguchi and I. Hirao, J. Org. Chem. (1985), 50, 1975 and R. C. Larock, Comprehensive Organic Transformations, Verlag Chemie, Weinheim 1989, p. 553 et seq. and the references in each case indicated therein).

Additional bases which can be used are, for example, pyrrolidine, tetrabutylammonium bromide or other organic nitrogen bases.

Normally, the reaction is carried out under atmospheric pressure or under the autogenous pressure of the respective solvent.

With reference to the reaction III→II→I, in addition to the references already cited above, reference may also be made to W. Flitsch and S. R. Schindler, Synthesis (1975), 685 and the literature cited therein.

A further possibility for preparing the compounds II is the reaction of a compound V with an aniline VI:

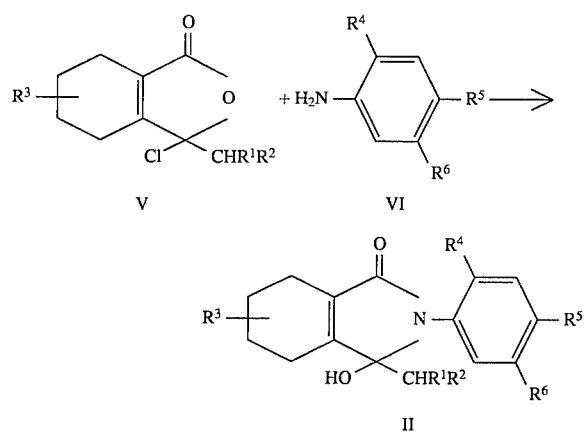

This reaction is expediently carried out in the manner described in R. Scheffold and P. Dabs, Helv. Chim. Acta (1967) 50, 794 and the references cited therein.

b) reaction of an aniline VI with a ketoacid VII, a lactol VIII or a lactone IX

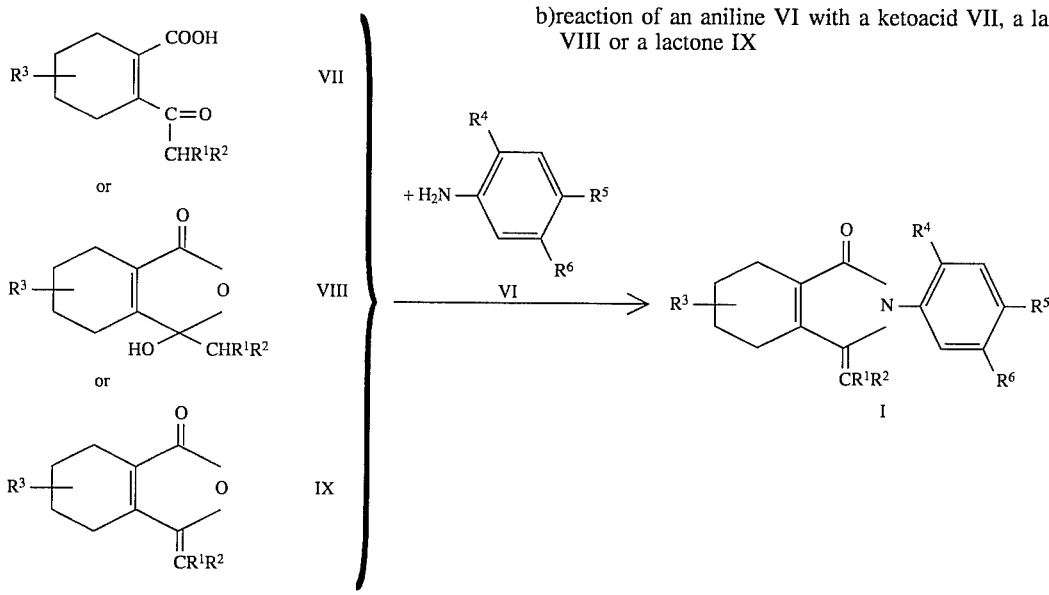

The reaction is carried out without solvent or in an inert solvent or diluent, preferably in the presence of an acidic catalyst.

Suitable solvents or diluents for this purpose are aliphatic and aromatic hydrocarbons such as n-hexane, toluene and xylene and also halogenated hydrocarbons, for example chlorobenzene and dichloromethane.

Suitable acidic catalysts are in particular protic acids, such as hydrochloric acid and sulfuric acid, sulfonic acids such as methanesulfonic acid, benzenesulfonic acid and p-toluenesulfonic acid, or acidic alkali metal sulfates such as sodium hydrogen sulfate and potassium hydrogen sulfate.

The proportions are not critical; in order to achieve a conversion to VII, VIII or IX which is as complete as possible, a one- to two-fold molar amount of VI is required.

The reaction temperature is in general from 20° to 200° C., preferably from 60° to 150° C.

The reaction can be carried out under atmospheric pressure or under superatmospheric pressure. Expediently, however, it is carried out under atmospheric pressure or under the autogenous pressure of the reaction mixture.

c) direct olefination of a 3,4,5,6-tetrahydrophthalimide III

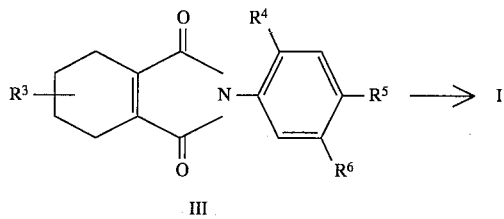

This method can only be used if $R^6$ is a substituent inert to the olefination. If, on the other hand, $R^6$ contains, for example, a carbonyl which can also be olefinated, this must be converted into a protective group, for example into an acetal, thioacetal or ketal, before the olefination reaction.

Suitable olefination reagents are in particular organophosphorus compounds, as are customarily used for the Wittig or Wittig-Horner reaction known per se, or, for example, the Tebbe-Grubbs reagent (complex of titanocene tetrachloride and trimethylaluminum), the Nozaki-Lombardo reagent (obtainable by addition of titanium tetrachloride to a suspension of zinc dust and a geminal dibromide in tetrahydrofuran at about –40° C., and also other transition metal carbene complexes, for example X or XI (cf. also R. C. Larock, Comprehensive Organic Transformations, p.180 et seq.):

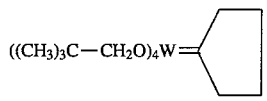

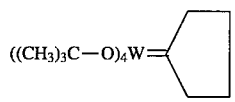

The reaction conditions for these processes can be taken, for example, from the following publications:

Houbel-Weyl, Lehrbuch der Organischen Chemie (Textbook of Organic Chemistry), Vol. E1, G. Thieme Verlag, Stuttgart 1982, p. 710 et seq.;
G. D. James et al., Tetrahedron Letters (1985) 26, 3617;
W. Flitsch and S. R. Schindler, Synthesis (1975) 685;
Murphy and Brenon, Chem. Soc. Rev. (1988) 17, 1;
L. F. Cannizzo, R. H. Grubbs, J. Org. Chem. (1985) 50, 2316;
A. Aguero et al., J. Chem. Soc. Chem. Commun. (1986), 531;
A. Toshimitsu, S. Uemuro, J. Chem. Soc. Chem. Commun. (1986), 530;
K. Takai et al., Tetrahedron Letters (1989) 30, 211;
J. P. Begue and D. Mesuaur, Synthesis (1989) 309;
For the preparation of the olefination reagents cf., in addition to the references cited above, for example:
H. Nozaki, Tetrahedron Letters (1985) 26, 5579 and 5581;
L. Lombardo, Tetrahedron Letters (1982) 23, 4293;
K. Takai, J. Org. Chem. (1987) 52, 4410;
F. N. Tebbe, J. Am. Chem. Soc. (1978) 100, 3611;
R. H. Grubbs et al., J. Org. Chem. (1990) 55, 843;
Ch. Eschenbroich and A. Salzer, Organometallchemie (Organometallic chemistry)Teubner 1988, p. 253 et seq. and the references in each case cited therein.

Depending on the particular substituents, it may be expedient first to convert one of the two carbonyl groups of the 3,4,5,6-tetrahydrophthalimide III into a thiocarbonyl group and then to react this with a suitable olefination reagent without isolation from the reaction mixture.

Suitable olefination reagents for this purpose are in particular dimethyl bromomalonate or diethyl bromomalonate, and a suitable sulfurizing reagent is $P_4S_{10}$ or 2,4-bis(4-methoxyphenyl)-1,3,2,4-dithiadiphosphetane-2,4-dithione (Lawesson's reagent).

The reaction is carried out in a manner known per se {cf., for example, J. S. Petersen et al., J. Am. Chem. Soc. (1984) 106, 4539 and S. C. Carey et al., Tetrahedron Lett. (1985) 26 5887}.

The 3,4,5,6-tetrahydrophthalimides III are known or obtainable by methods known per se (cf., for example, DE-A 36 03 789, DE-A 36 07 300, DE-A 37 41 273, EP-A 177 032, EP-A 188 259, EP-A 207 894, EP-A 218 972, EP-A 263 299, EP-A 271 170, EP-A 275 131, EP-A 290 863, EP-A 296 416, EP-A 300 307, EP-A 300 387, EP-A 300 398, JA 60/152 465, JA 60/246 367, JA 59/155 358, JA 61/027 962, JA 62/114 961, JA 61/165 383, JA 63/267 779, JA 63/275 580, JA 61/174 970, JA 01/034 982, JA 01/047 784 and JA 01/066 182).

In general, they can be prepared by condensation of a compound VI with tetrahydrophthalic anhydrides XIII:

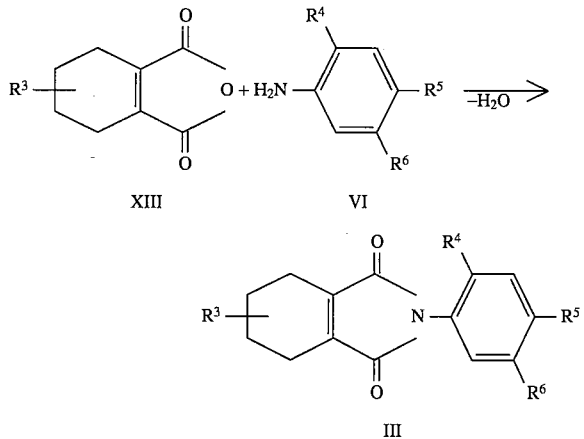

For the condensation, inert organic solvents such as lower alkanoic acids, for example acetic acid, propionic acid and isobutyric acid, and also the esters of these acids, such as ethyl acetate, higher-boiling hydrocarbons such as toluene and xylene and/or dimethylformamide are used as solvents.

The reaction is normally carried out at from 0° C. to the boiling point of the respective reaction mixture, preferably from 25° to 140° C. When using an aprotic solvent, it is recommended to remove the water continuously.

It may additionally be advantageous to carry out the condensation in the presence of an organic protic acid such as p-toluenesulfonic acid or benzenesulfonic acid.

Normally, the condensation is carried out at atmospheric pressure.

The compounds VI are also known or can be prepared by methods known per se, for example by reduction of the corresponding nitroaromatic.

Suitable reductants are, for example transition metals such as iron, hydrogen in the presence of a suitable catalyst such as Raney nickel or platinum on active carbon or complex metal halides such as sodium borohydride in the presence of a suitable catalyst, expediently a commercially available noble metal catalyst (cf., for example, T. Neilson et al., J. Chem. Soc. (1962), 371 and references cited therein).

Reduction and condensation can be carried out without isolation of VI.

The compounds VII, VIII, IX and V are also known or can be prepared by known methods {cf., for example, R. Scheffold and D. Dabs, Helv. Chim. Acta (1967) 50, 798, EP-A 420 810, EP-A 305 333 and DE-A 3 920 271 and the references cited in each case}.

As a rule, the substituted isoindolones I can be prepared by one of the abovementioned synthesis processes. For economical or process engineering reasons, however, it may be more expedient to prepare some compounds I from similarly substituted isoindolones I which differ, however, in particular in the meanings of the radicals $R^1$, $R^2$ and/or $R^6$, in a manner known per se, for example by ester hydrolysis, esterification, amidation, acetalisation, acetal hydrolysis, condensation reaction, Wittig reaction, Peterson olefination, etherification, alkylation, oxidation or reduction.

The substituted isoindolones can be obtained in the processes described above as isomer mixtures. Especially when $R^1$ and $R^2$ do not have the same meaning, E/Z isomer mixtures are obtained.

The isomers obtained, however, can be separated into the pure isomers, if desired using the methods customary for this purpose, for example by crystallization, chromatography (LC, HPLC, etc), if appropriate on an optically active absorbate (for this compare Example 4, compound Ic.13; separation method=LC).

Mixtures of optically active isomers I which contain one isomer in an excess can also be prepared, for example, using optically active starting materials.

Both the substituted isoindolones I and the hydroxyisoindolones II are suitable both as isomer mixtures and in the form of the pure isomers as herbicides and as defoliants/desiccants.

PREPARATION EXAMPLES

Example 1

2-[4-Chloro-4-(2-chloro-2-ethoxycarbonylethenyl)phenyl]-3-hydroxy-3-methyl-2,3,4,5,6,7-hexahydroisoindol-1-one (Compound IIa. 13)

1.21 g of magnesium turnings were reacted with 4.4 ml of methyl iodide in 30 ml of diethyl ether. A solution of 7.8 g of N-[4-chloro-3-(2-chloro-2-ethoxycarbonylethenyl)phenyl]-3,4,5,6-tetrahydrophthalimide in 130 ml of diethyl ether was added dropwise at 10° C. to the solution of methylmagnesium iodide obtained. The reaction mixture was then stirred for a further 1 hour at boiling point, after which it was poured into 300 ml of saturated ammonium chloride solution. The organic phase was then separated off and concentrated.

The crude product was employed in the following step without further purification.

Example 2

2-[4-Chloro-3-(2-chloro-2-ethoxycarbonylethenyl)phenyl]-3-methylidene-4,5,6,7-tetrahydro-2H-isoindon-1-one (Compound Ia. 13)

A solution of the 2-[4-chloro-3-(2-chloro-2-ethoxycarbonylethenyl)phenyl]-3-hydroxy-3-methyl-2,3,4,5,6,7-hexahydroisoindon-1-one obtained as described in Example 1 was treated with 0.1 g of p-toluenesulfonic acid in 150 ml of toluene. The mixture was heated to boiling point for two hours, then cooled and concentrated under reduced pressure.

The crude product was purified by means of chromatography on silica gel (using dichloromethane as the eluent) and purified by subsequent stirring with petroleum ether. Yield: 4.5 g; m.p. 85°–86° C.

Example 3

2-[4-Chloro-4-(2-chloro-2-ethoxycarbonylethenyl)phenyl]-3-ethyl-3-hydroxy-2,3,4,5,6,7-hexahydroisoindol-1-one (Compound IIc.13)

1.21 g of magnesium turnings were reacted with 5.74 ml of ethyl iodide in 30 ml of diethyl ether. The solution of ethylmagnesium iodide obtained was added dropwise at 10° C. to a solution of 7.8 g of N-[4-chloro-3-(2-chloro-2-ethoxycarbonylethenyl)phenyl]-3,4,5,6-tetrahydrophthalimide in 130 ml of diethyl ether. After heating to reflux temperature for 1.5 hours, the reaction mixture was added to 300 ml of saturated aqueous ammonium chloride solution. The organic phase was then separated off, dried over sodium sulfate and concentrated under reduced pressure.

One half of the crude product obtained was further reacted as described in Example 4; the other half was purified by chromatography on silica gel (eluent: 1, dichloromethane; 2, dichloromethane/ethyl acetate 4:1), 1.2 g of the product being obtained; m.p.: 64°–67° C.

Example 4

2-[4-Chloro-3-(2-chloro-2-ethoxycarbonylethenyl)phenyl]-3-ethylidene-4,5,6,7-tetrahydro-2H-isoindol-1-one (Compound Ic. 13)

A solution of the 2-[4-chloro-4-(2-chloro-2-ethoxycarbonylethenyl)phenyl]-3-ethyl-3-hydroxy-2,3,4,5,6,7-hexahydroisoindol-1-one (Compound IIc.13; unpurified) obtained as described in Example 3 was treated with 0.1 g of p-toluenesulfonic acid in 150 ml of toluene. After heating to reflux temperature for 2 hours, the solvent was removed under reduced pressure. The residue was purified by chromatography on silica gel (eluent: 1, toluene; 2, dichloromethane).

Yield: 1.1 g of 2-[4-chloro-3-(2-chloro-2-ethoxycarbonylethenyl)phenyl]-3Z*)-ethylidene-4,5,6,7-tetrahydro-2H-isoindol-1-one and 0.9 g of 2-[4-Chloro-3-(2-chloro-2-ethoxycarbonylethenyl)phenyl]-3E*)-ethylidene-4,5,6,7-tetrahydro-2H-isoindol-1-one

*)Structure assignment by means of $^1$H-NMR (see Table 21)

Example 5

2-[4-Chloro-3-(4-methyl-1,3-dithiolan-2-yl)phenyl]-3-(ethoxycarbonylethylidene)-4,5,6,7-tetrahydro-2H-isoindol-1-one 1.75 g of (ethoxycarbonylmethylene)triphenylphosphorane were added to a solution of 1.90 g of 2-[4-chloro-3-(4-methyl-1,3-dithiolan-2-yl)phenyl]-4,5,6,7-tetrahydro-2H-isoindol-1,3-dione in 50 ml of toluene. The solution obtained was then refluxed for 5 hours, after which a further 5.25 g of (ethoxycarbonylmethylene)triphenylphosphorane were added in two portions. The reaction mixture was refluxed for a total of 6 hours and then cooled to about 25° C. After separating off solid components and solvent, the residue was treated with diisopropyl ether. The substance crystallizing from diisopropyl ether was separated off and the filtrate was chromatographed on silica gel (eluent: $CH_2Cl_2$). Yield : 0.7 g of the title compound as an 85:15 E/Z isomer mixture.

In the following tables 17 and 18, particularly preferred substituted isoindolones I are shown which were prepared or can be prepared in the same manner:

TABLE 17

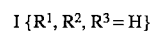

I {$R^1$, $R^2$, $R^3$ = H; $R^5$ = Cl}

| No. | $R^4$ | $R^6$ | M.p. [°C.] |
|---|---|---|---|
| Ia.01 | H | CH=CH—CN | |
| Ia.02 | F | CH=CH—CN | |
| Ia.03 | H | CH=C(CH₃)—CN | |
| Ia.04 | F | CH=C(CH₃)—CN | |
| Ia.05 | H | CH=CH—COOCH₃ | |
| Ia.06 | F | CH=CH—COOCH₃ | |
| Ia.07 | H | CH=CH—COOC₂H₅ | oil |
| Ia.08 | F | CH=CH—COOC₂H₅ | |
| Ia.09 | H | CH=C(CN)—COOCH₃ | |
| Ia.10 | F | CH=C(CN)—COOCH₃ | |
| Ia.11 | H | CH=C(Cl)—COOCH₃ | |
| Ia.12 | F | CH=C(Cl)—COOCH₃ | |
| Ia.13 | H | CH=C(Cl)—COOC₂H₅ | 85–86 |
| Ia.14 | F | CH=C(Cl)—COOC₂H₅ | |
| Ia.15 | H | CH=C(Br)—COOCH₃ | 76–78 |
| Ia.16 | F | CH=C(Br)—COOCH₃ | |
| Ia.17 | H | CH=C(Br)—COOC₂H₅ | |
| Ia.18 | F | CH=C(Br)—COOC₂H₅ | |
| Ia.19 | H | CH₂—CN | |
| Ia.20 | F | CH₂—CN | |
| Ia.21 | H | CH₂—CH₂—COOCH₃ | |
| Ia.22 | F | CH₂—CH₂—COOCH₃ | |
| Ia.23 | H | CH₂—CH₂—COOC₂H₅ | |
| Ia.24 | F | CH₂—CH₂—COOC₂H₅ | |
| Ia.25 | H | CH₂—CH(CN)—COOCH₃ | |
| Ia.26 | F | CH₂—CH(CN)—COOCH₃ | |
| Ia.27 | H | CH₂—CH(Cl)—COOCH₃ | |
| Ia.28 | F | CH₂—CH(Cl)—COOCH₃ | |
| Ia.29 | H | CH₂—C(Cl)—COOC₂H₅ | |
| Ia.30 | F | CH₂—C(Cl)—COOC₂H₅ | |
| Ia.31 | H | CH₂—C(Br)—COOCH₃ | |
| Ia.32 | F | CH₂—C(Br)—COOCH₃ | |
| Ia.33 | H | CH₂—C(Br)—COOC₂H₅ | |
| Ia.34 | F | CH₂—C(Br)—COOC₂H₅ | |
| Ia.35 | H | 1,3-dioxolan-2-yl | |
| Ia.36 | F | 1,3-dioxolan-2-yl | |
| Ia.37 | H | 1,3-dioxan-2-yl | 103–105 |
| Ia.38 | F | 1,3-dioxan-2-yl | |
| Ia.39 | H | 1,3-dithiolan-2-yl | |
| Ia.40 | F | 1,3-dithiolan-2-yl | |
| Ia.41 | H | 1,3-dithian-2-yl | |
| Ia.42 | F | 1,3-dithian-2-yl | |
| Ia.43 | H | 4-CH₃-1,3-dithiolan-2-yl | 110–112 |
| Ia.44 | F | 4-CH₃-1,3-dithiolan-2-yl | |
| Ia.45 | H | CH(OCH₃)₂ | |
| Ia.46 | F | CH(OCH₃)₂ | |
| Ia.47 | H | CH(OC₂H₅)₂ | |
| Ia.48 | F | CH(OC₂H₅)₂ | |
| Ia.49 | H | CH=N—OCH₂—COOCH₃ | |
| Ia.50 | F | CH=N—OCH₂—COOCH₃ | |
| Ia.51 | H | CH=N—OH | |
| Ia.52 | F | CH=N—OH | |
| Ia.53 | H | CH=N—OCH(CH₃)—COOCH₃ | |
| Ia.54 | F | CH=N—OCH(CH₃)—COOCH₃ | |
| Ia.55 | H | CH=N—OCH(CH₃)—COOC₂H₅ | |
| Ia.56 | F | CH=N—OCH(CH₃)—COOC₂H₅ | |

TABLE 18

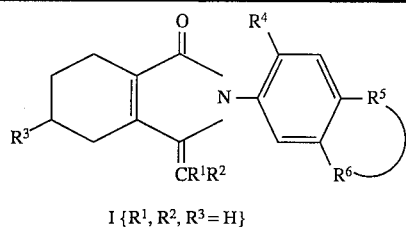

I {$R^1$, $R^2$, $R^3$ = H}

| No. | $R^4$ | —($R^5$—$R^6$)— | M.p. [°C.] |
|---|---|---|---|
| Ib.01 | H | —O—CH₂—CO—N(CH₃)— | |
| Ib.02 | H | —O—CH₂—CO—N—(CH₂C≡CH)— | |
| Ib.03 | H | —O—CH₂—CO—N(CH(CH₃)C≡CH)— | |
| Ib.04 | H | —O—CH(CH₃)—N(CH₃)— | |
| Ib.05 | H | —O—CH(CH₃)—CO—N(CH₂C≡CH)— | |
| Ib.06 | H | —S—CH₂—CO—N(CH₃)— | |
| Ib.07 | F | —S—CH₂—CO—N(CH₃)— | |
| Ib.08 | H | —S—CH₂—CO—N(CH₂C≡CH)— | |
| Ib.09 | F | —S—CH₂—CO—N(CH₂C≡CH)— | |
| Ib.10 | H | —CH₂—CH₂—CO—N(CH₂C≡CH)— | |
| Ib.11 | F | —CH₂—CH₂—CO—N(CH₂C≡CH)— | |
| Ib.12 | H | —O—CO—N(CH₂C≡CH)— | |
| Ib.13 | F | —O—CO—N(CH₂C≡CH)— | |
| Ib.14 | H | —S—CO—N(CH₂C≡CH)— | |
| Ib.15 | F | —S—CO—N(CH₂C≡CH)— | |
| Ib.16 | H | —CH₂—CO—N(CH₂C≡CH)— | |
| Ib.17 | F | —CH₂—CO—N(CH₂C≡CH)— | |
| Ib.18 | H | —N=CH—CO—N(CH₂C≡CH)— | |
| Ib.19 | F | —N=CH=CO=N(CH₂C≡CH)— | |

In addition, the following substituted isoindolones I are particularly preferred:

the compounds Nos. Ic.01 to Ic.56, which differ from the compounds Nos. Ia.01 to Ia.56 in that $R^1$ is in each case methyl;

the compounds Nos. Id.01 to Id.56, which differ from the compounds Nos. Ia.01 to Ia.56 in that $R^1$ is in each case ethyl;

the compounds Nos. Ie.01 to Ie.56, which differ from the compounds Nos. Ia.01 to Ia.56 in that $R^1$ is in each case n-propyl;

the compounds Nos. If.01 to If.56, which differ from the compounds Nos. Ia.01 to Ia.56 in that $R^1$ is in each case n-pentyl;

the compounds Nos. Ig.01 to Ig.56, which differ from the compounds Nos. Ia.01 to Ia.56 in that $R^1$ is in each case phenyl;

the compounds Nos. Ih.01 to Ih.19, which differ from the compounds Nos. Ib.01 to Ib.19 in that $R^1$ is in each case methyl;

the compounds Nos. Ii.01 to Ii.19, which differ from the compounds Nos. Ib.01 to Ib.19 in that $R^1$ is in each case ethyl;

the compounds Nos. Ik.01 to Ik.56, which differ from the compounds Nos. Ia.01 to Ia.56 in that $R^1$ is in each case ethoxycarbonyl.

The following tables 19 and 20 contain hydroxyindolones II of the invention which are particularly preferred:

TABLE 19

I {$R^1$, $R^2$, $R^3$ = H; $R^5$ = Cl}

| No. | $R^4$ | $R^6$ | M.p. [°C.] |
|---|---|---|---|
| IIa.01 | H | CH=CH—CN | |
| IIa.02 | F | CH=CH—CN | |
| IIa.03 | H | CH=C(CH$_3$)—CN | |
| IIa.04 | F | CH=C(CH$_3$)—CN | |
| IIa.05 | H | CH=CH—COOCH$_3$ | |
| IIa.06 | F | CH=CH—COOCH$_3$ | |
| IIa.07 | H | CH=CH—COOC$_2$H$_5$ | 150–152 |
| IIa.08 | F | CH=CH—COOC$_2$H$_5$ | |
| IIa.09 | H | CH=C(CN)—COOCH$_3$ | |
| IIa.10 | F | CH=C(CN)—COOCH$_3$ | |
| IIa.11 | H | CH=C(Cl)—COOCH$_3$ | |
| IIa.12 | F | CH=C(Cl)—COOCH$_3$ | |
| IIa.13 | H | CH=C(Cl)—COOC$_2$H$_5$ | |
| IIa.14 | F | CH=C(Cl)—COOC$_2$H$_5$ | |
| IIa.15 | H | CH=C(Br)—COOCH$_3$ | 60–70 (dec.) |
| IIa.16 | F | CH=C(Br)—COOCH$_3$ | |
| IIa.17 | H | CH=C(Br)—COOC$_2$H$_5$ | |
| IIa.18 | F | CH=C(Br)—COOC$_2$H$_5$ | |
| IIa.19 | F | CH$_2$—CN | |
| IIa.20 | F | CH$_2$—CN | |
| IIa.21 | H | CH$_2$—CH$_2$—COOCH$_3$ | |
| IIa.22 | F | CH$_2$—CH$_2$—COOCH$_3$ | |
| IIa.23 | H | CH$_2$—CH$_2$—COOC$_2$H$_5$ | |
| IIa.24 | F | CH$_2$—CH$_2$—COOC$_2$H$_5$ | |
| IIa.25 | H | CH$_2$—CH(CN)—COOCH$_3$ | |
| IIa.26 | F | CH$_2$—CH(CN)—COOCH$_3$ | |
| IIa.27 | H | CH$_2$—CH(Cl)—COOCH$_3$ | |
| IIa.28 | F | CH$_2$—CH(Cl)—COOCH$_3$ | |
| IIa.29 | H | CH$_2$—C(Cl)—COOC$_2$H$_5$ | |
| IIa.30 | F | CH$_2$—C(Cl)—COOC$_2$H$_5$ | |
| IIa.31 | H | CH$_2$—C(Br)—COOCH$_3$ | |
| IIa.32 | F | CH$_2$—C(Br)—COOCH$_3$ | |
| IIa.33 | H | CH$_2$—C(Br)—COOC$_2$H$_5$ | |
| IIa.34 | F | CH$_2$—C(Br)—COOC$_2$H$_5$ | |
| IIa.35 | H | 1,3-dioxolan-2-yl | |
| IIa.36 | F | 1,3-dioxolan-2-yl | |
| IIa.37 | H | 1,3-dioxan-2-yl | 163–165 |
| IIa.38 | F | 1,3-dioxan-2-yl | |
| IIa.39 | H | 1,3-dithiolan-2-yl | |
| IIa.40 | F | 1,3-dithiolan-2-yl | |
| IIa.41 | H | 1,3-dithian-2-yl | |
| IIa.42 | F | 1,3-dithian-2-yl | |
| IIa.43 | F | 4-CH$_3$-1,3-dithiolan-2-yl | 110–112 |
| IIa.44 | H | 4-CH$_3$-1,3-dithiolan-2-yl | |

TABLE 20

I {$R^1$, $R^2$, $R^3$ = H}

| No. | $R^4$ | —($R^5$—$R^6$)— | M.p. [°C.] |
|---|---|---|---|
| IIb.01 | H | —O—CH$_2$—CO—N(CH$_3$)— | |
| IIb.02 | F | —O—CH$_2$—CO—N(CH$_2$C≡CH)— | |
| IIb.03 | H | —O—CH(CH$_3$)—N(CH$_3$)— | |
| IIb.04 | F | —O—CH(CH$_3$)—CO—N(CH$_2$C≡CH)— | |
| IIb.05 | H | —S—CH$_2$—CO—N(CH$_3$)— | |
| IIb.06 | F | —S—CH$_2$—CO—N(CH$_3$)— | |
| IIb.07 | H | —S—CH$_2$—CO—N(CH$_2$C≡CH)— | |
| IIb.08 | F | —S—CH$_2$—CO—N(CH$_2$C≡CH)— | |
| IIb.09 | H | —CH$_2$—CH$_2$—CO—N(CH$_2$C≡CH)— | |
| IIb.10 | F | —CH$_2$—CH$_2$—CO—N(CH$_2$C≡CH)— | |
| IIb.11 | H | —O—CO—N(CH$_2$C≡CH)— | |
| IIb.12 | F | —O—CO—N(CH$_2$C≡CH)— | |
| IIb.13 | H | —S—CO—N(CH$_2$C≡CH)— | |
| IIb.14 | F | —S—CO—N(CH$_2$C≡CH)— | |
| IIb.15 | H | —CH$_2$—CO—N(CH$_2$C≡CH)— | |
| IIb.16 | F | —CH$_2$—CO—N(CH$_2$C≡CH)— | |
| IIb.17 | H | —N=CH—CO—N(CH$_2$C≡CH)— | |
| IIb.18 | F | —N=CH—CO—N(CH$_2$C≡CH)— | |

In addition, the following hydroxyisoindolones II are particularly preferred:

the compounds IIc.01 to IIc.44, which differ from the compounds IIa.01 to IIa.44 in that $R^1$ is methyl;

the compounds IId.01 to IId.44, which differ from the compounds IIa.01 to IIa.44 in that $R^1$ is ethyl;

the compounds IIe.01 to IIe.44, which differ from the compounds IIa.01 to IIa.44 in that $R^1$ is n-propyl;

the compounds IIf.01 to IIf.44, which differ from the compounds IIa.01 to IIa.44 in that $R^1$ is n-pentyl;

the compounds IIg.01 to IIg.44, which differ from the compounds IIa.01 to IIa.44 in that $R^1$ is phenyl;

the compounds IIh.01 to IIh.18, which differ from the compounds IIb.01 to IIb.18 in that $R^1$ is methyl;

the compounds IIi.01 to IIi.18, which differ from the compounds IIb.01 to IIb.18 in that $R^1$ is ethyl.

Physical data of compounds I and II are evident from the following Table 21:

TABLE 21

| Compound No. | M.p. or spectroscopic data (IR [cm$^{-1}$]; $^1$H-NMR [ppm]) |
|---|---|
| Ia.07 | Oil, IR: ν = 1712, 1636, 1474, 1420, 1379, 1367, 1314, 1265, 1180, 1042 |
| Ic.13 | E-isomer; oil; NMR (CDCl$_3$, 250 MHz): δ = 1.39 (t, 3H); 1.66–1.89 (m, 4H); 1.98 (d, 3H); 2.33–2.47 (m, 2H); 2.65–2.78 (m, 2H); 4.37 (q); 5.36 (q); 7.16–7.83 (m, 3H); 8.15 (s, 1H); Z-isomer; oil; NMR (CDCl$_3$, 250 MHz): δ = 1.39 (t, 3H); 1.41 (d, 3H); 1.68–1.85 (m, 4H); 2.28–2.45 (m, 4H); 4.37 (q, 3H); 5.25 (q, 3H); 7.12–7.88 (m, 3H); 8.14 (s, 1H) |
| Ic.43 | oil, IR: ν = 2931, 1697, 1659, 1471, 1413, 1390, 1371, 1122, 1067, 1039 |
| Id.43 | oil, IR: ν = 2962, 2931, 2869, 1698, 1471, 1412, 1387, 1158, 1118, 1039 |
| If.43 | oil, IR: ν = 2952, 2927, 2856, 1699, 1470, 1435, 1413, 1387, 1123, 1041 |
| Ik.43 | oil; NMR (CDCL$_3$: δ = 1.24 (t, 3H); 1.49 (2d, 3H); 1.77 (bs, 4H); 2.33–2.50 (2H); 2.75–2.84 (2H); 2.96–3.10 (mk, 1H); 3.23–3.45 (mk, 1H); 3.88–4.03 (mk, 1H); 4.93 (q, 2H); 5.44 (2s, 1H); 6.03 (s, 1H); 7.01–7.10, 7.42–7.48, 7.72–7.84 (3H) |
| IIc.13 | 64 to 67° C. |
| IIc.43 | 151 to 153° C. |
| IId.43 | 147 to 148° C. |
| IIf.43 | oil, IR: ν = 3350, 2928, 2857, 1679, 1472, 1422, 1397, 1372, 1071, 1052 |

The substituted isoindolones I and hydroxyisoindolones II are useful, both as isomer mixtures and in the form of the pure isomers, as herbicides, in particular for controlling dicotyledon weeds. In particular at low application rates, they are tolerable and thus selective in cultures such as wheat, rice, corn, soya and cotton.

The substituted isoindolones I and hydroxyisoindolones II are additionally useful as desiccants and defoliants, in particular for defoliating cotton, and as defoliants for drying the above-ground parts of plants in cultivated plants, for example potato, sunflower, soya bean and rape. Completely mechanised harvesting of these important cultivated plants is thus made possible.

Of economical interest is additionally the facilitation of harvesting, which is made possible by the temporally concentrated dropping of the fruit or reduction in its power of adhesion to the tree in the case of citrus fruits, olives or other varieties and types of pomiferous, drupaceous and indehiscent fruit trees. Additionally, the compounds lead to a uniform ripening-off of the harvested fruit.

The same mechanism, ie. the promotion of the formation of separating tissue between the fruit or leaf and stem part of the plant is also essential for a readily controllable defoliation of useful plants such as, in particular, cotton. Additionally, the shortening of the time interval in which the individual cotton plants become ripe leads to an increased fiber quality after harvesting.

The compounds I and II or the herbicides or desiccants/defoliants containing them can be used, for example, in the form of directly sprayable solutions, powders, suspensions, including high-percentage aqueous, oily or other suspensions or dispersions, emulsions, oil dispersions, pastes, dusts, broadcasting agents or granules by spraying, atomizing, dusting, scattering or pouring. The application forms depend on the intended use; in each case, if possible, they should ensure the finest dispersion of the active compounds.

The compounds I and II are generally suitable for the preparation of directly sprayable solutions, emulsions, pastes or oil dispersions. Suitable inert additives are mineral oil fractions of medium to high boiling point, such as kerosene or diesel oil, and also coal-tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by the addition of water. For the preparation of emulsions, pastes or oil dispersions, the substrates can be homogenized in water as such or in an oil or solvent by means of wetting agents, tackifiers, dispersants or emulsifiers. However, concentrates consisting of active substance, wetting agent, tackifer, dispersant or emulsifier and possibly solvent or oil which are suitable for dilution with water can also be prepared.

Suitable surface-active substances are the alkali metal, alkaline earth metal or ammonium salts of aromatic sulfonic acids, for example lignin-, phenol-, naphthalene and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or naphthalenesulfonic acids with phenol and formaldehyde, polyoxyethylene octylphenol ether, ethoxylated isooctyl-, octyl- or nonylphenol, alkylphenol or tributylphenyl polyglycol ether, alkylaryl polyether alcohols, isotridecyl alcohol, fatty alcohol ethylene oxide condensates, ethoxylated castor oil, polyoxyethylene alkyl ether or polyoxypropylene, lauryl alcohol polyglycol ether acetate, sorbitol ester, lignin-sulfite waste liquors or methyl cellulose.

Powders, broadcasting agents and dusts can be prepared by mixing or grinding of the active substances together with a solid carrier.

Granules, e.g. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and plant products, such as cereal flour, tree bark, wood and nutshell meal, cellulose powder or other solid carriers.

The formulations in general contain from 0.01 to 95% by weight, preferably from 0.5 to 90% by weight, of active compound. The active compounds are in this case employed in a purity of 90%–100%, preferably 95%–100% (by NMR spectrum).

Examples of such preparations are:

I. a mixture of 20 parts by weight of compound No. Ia.07, 80 parts by weight of xylene, 10 parts by weight of the addition products of 8–10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil. By fine dispersion of the mixture in 100,000 parts by weight of water, an aqueous dispersion is obtained which contains 0.02% by weight of the active compound;

II. a dispersion of 20 parts by weight of the compound, No. Ia.43, in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of caster oil. The mixture of this dispersion with 100,000 parts by weight of water contains 0.02% by weight of the active compound;

III. a dispersion of 20 parts by weight of compound No. Id.43, in a mixture of 25 parts by weight of cyclohexanone, 65 parts by weight of a mineral oil fraction of boiling point 210°–280° C. and 10 parts by weight of the addition product of 40 mol of ethylene oxide to 1 mol of castor oil. The mixture of this dispersion with 100,000 parts by weight of water contains 0.02 % by weight of the active compound;

IV. a mixture, ground in a hammer mill, of 20 parts by weight of compound No. IIc.13, 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel. By fine dispersion of the mixture in 20,000 parts by weight of water, a spray liquor is obtained which contains 0.1% by weight of the active compound;

V. an intimate mixture of 3 parts by weight of compound No. IIc.43 and 97 parts by weight of finely divided kaolin. This dust contains 3% by weight of active compound;

VI. a stable oily dispersion of 20 parts by weight of compound No. IIf.43, 2 parts by weight of the calcium salt of dodecylbenzenesulfonic acid, 8 parts by weight of fatty alcohol polyglycol ether, 2 parts by weight of the sodium salt of a phenolsulfonic acid-urea formaldehyde condensate and 68 parts by weight of a paraffinic mineral oil.

The application of the herbicides or of the active compounds can be carried out pre-emergence or post-emergence. If the active compounds are less tolerable to certain crop plants, application techniques can be used in which the herbicides are sprayed with the aid of spraying equipment such that the leaves of the sensitive crop plants are not affected if possible, while the active compounds reach the leaves of undesired plants growing underneath or the uncovered soil surface (post-directed, lay-by).

The application rates of active compound are, depending on the control target, time of year, target plants and stage of growth, from 0.001 to 3.0, preferably from 0.01 to 1 kg/ha of active substance (a.s.).

In view of the versatility of the application methods, the compounds I and II or compositions containing them can additionally be employed in a further number of crop plants for the elimination of undesired plants. The following crops, for example, are suitable:

| Botanical Name | Common Name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugar beets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | turnips |
| *Camellia sinensis* | tea plants |
| *Carthamus tinctorius* | safflower |
| *Carya illinoinensis* | pecan trees |
| *Citrus limon* | lemons |
| *Citrus senensis* | orange trees |
| *Coffea arabica* (*Coffea canephora, Coffea liberica*) | coffee |
| *Cucumis sativus* | cucumbers |
| *Cynodon dactylon* | Bermuda grass |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | Lima beans |
| *Phaseolus vulgaris* | snap beans, green beans, dry beans |
| *Picea abies* | Norway spruce |
| *Pinus* spp. | pine trees |
| *Pisum staivum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*S. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

To widen the spectrum of action and to obtain synergistic effects, the compounds I and II can be mixed with numerous representatives of other herbicidal or growth-regulating active compound groups and applied together. For example, suitable mixture components are diazines, 4H- 3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane- 1,3-dione derivatives which in the 2 position carry e.g. a carboxyl or carbimino group, quinoline- carboxylic acid derivatives, imidazolinones, sulfonamides, sulfonylureas, aryloxy- and hetaryloxyphenoxypropionic acids and their salts, esters and amides and others.

Additionally, it may be useful to apply the compounds I and II on their own or together in combination with other herbicides, also additionally mixed with other crop protection compositions, for example with compositions for controlling pests or phytopathogenic fungi or bacteria. Also of interest is the miscibility with mineral salt solutions which are used for rectifying nutritional and trace element deficiencies. However, non-phytotoxic oils and oil concentrates can also be added.

USE EXAMPLES (herbicidal activity)

The herbicidal action of the substituted isoindolones I and hydroxyisoindolones II could be shown by greenhouse tests:

The cultivation containers used were plastic flowerpots containing loamy sand with about 3.0% by weight of humus as substrate. The seeds of the test plants were sown separately according to variety.

In the case of pre-emergence treatment, the active compounds suspended or emulsified in water were applied directly after sowing by means of finely dividing nozzles. The containers were lightly watered in order to promote germination and growth and then covered with transparent plastic caps until the plants had taken root. This covering caused uniform germination of the test plants inasmuch as this was not affected by the active compounds.

For the purpose of post-emergence treatment, the test plants were grown, depending on form of growth, up to a height of growth of from 3 to 15 cm and only then treated with the active compounds suspended or emulsified in water. The test plants were either sown and grown in the test containers in which they were treated, or they were grown separately as seed plants and transplanted into the test containers a few days before the treatment with the active compound preparations.

The application rate for post-emergence treatment was 0.5 kg/ha a.s.

The plants were kept according to variety at temperatures of from 10° to 25° C. or from 20° to 35° C. The test period ranged from 2 to 4 weeks. During this time, the plants were cared for and their reaction to the individual treatments was assessed.

Assessment was carried out on a scale from 0 to 100. In this, 100 means no emergence of the plants or complete destruction at least of the above-ground parts and 0 means no damage or a normal course of growth.

The plants used in the greenhouse tests consisted of the following varieties:

| Latin Name | English name |
| --- | --- |
| Abutilon theophrasti | velvet leaf |
| Amaranthus retroflexus | redroot pigweed |
| Galium aparine | catchweed bedstraw |
| Chenopodium album | lambsquarters (goosefoot) |
| Ipomoea subspecies | morning-glory |
| Solanum nigrum | black nightshade |

The result showed that undesired weeds can be very well controlled using the compounds Nos. Ia.13, Ia.43 and Ic.13 (E- and Z- isomer with respect to $R^1$).

We claim:

1. A substituted isoindolone of the formula I

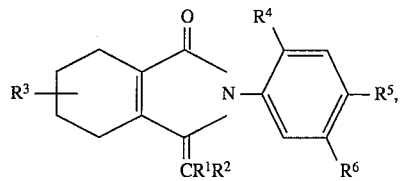

where the variables have the following meanings:

$R^1$ and $R^2$ are
hydrogen, $C_1$–$C_6$-alkyl, $C_2$–$C_6$-alkenyl, $C_2$–$C_6$-alkynyl, tri-($C_1$–$C_6$-alkyl)silyl-$C_2$–$C_6$-alkynyl, $C_1$–$C_6$-alkoxy-$C_1$–$C_6$-alkyl, cyano, $C_1$–$C_6$-cyanoalkyl, $C_1$–$C_6$-alkoxycarbonyl, formyl, $C_1$–$C_6$-alkylcarbonyl, phenylcarbonyl where the phenyl ring may be unsubstituted or may be substituted by one to three radicals selected from the group consisting of $C_1$–$C_6$-alkyl, $C_1$–$C_6$-alkoxy, halogen, cyano, nitro and trifluoromethyl, $C_1$–$C_6$-alkoxycarbonyl-$C_1$–$C_6$-alkyl, $C_1$–$C_6$-alkoxycarbonyl-$C_2$–$C_6$-alkenyl, $C_3$–$C_8$-cycloalkyl and $C_1$–$C_6$-haloalkyl, or, if $R^1$ is hydrogen, $R^2$ is additionally phenyl which may be unsubstituted or may be substituted by one to three radicals selected from the group consisting of $C_1$–$C_6$-alkyl, $C_1$–$C_6$-alkoxy, halogen, cyano, nitro and trifluoromethyl, or $R^1$ and $R^2$, together with the common C atom to which they are bonded, form a three- to eight-membered saturated or unsaturated non-aromatic carbo- or heterocycle which ring may contain one to three N atoms and an additional oxygen or sulfur atom and also one or two carbonyl groups as ring members, which ring may be substituted by one to three identical or different $C_1$–$C_6$-alkyl groups;

$R^3$ is
hydrogen or $C_1$–$C_6$-alkyl;

$R^4$ is
hydrogen or halogen;

$R^5$ is
hydrogen, halogen, nitro, cyano or trifluoromethyl;

$R^6$ is
a 3- to 8-membered heterocyclyl which may be saturated or partially or completely unsaturated and may optionally contain one to four heteroatoms selected from the group consisting of one to four nitrogen atoms, one or two oxygen atoms and one or two sulfur atoms, where the heterocycle may optionally be substituted by one of the following substituents on each substitutable atom: $C_1$–$C_6$-alkyl, $C_2$–$C_6$-alkenyl, halogen, cyano, nitro, $C_1$–$C_6$-haloalkyl, $C_1$–$C_6$-alkoxy or $C_1$–$C_6$-alkoxycarbonyl, or one of the following groups: —A—CN, —A—CO—B, —C($R^{10}$)=O, —C($R^{10}$)=S, —C($R^{10}$)=N—$R^{11}$, —C($X^1R^{14}$)($X^2R^{15}$)$R^{10}$, —P($R^{12}$)($R^{13}$)=O, where A is
a $C_1$–$C_4$-alkylene, $C_2$–$C_4$-alkenylene or $C_2$–$C_4$-alkynylene chain which may in each case be unsubstituted or may optionally be substituted by one or two radicals selected from the group consisting of halogen, cyano, $C_1$–$C_6$-alkyl, $C_1$–$C_6$-alkoxycarbonyl and $C_1$–$C_6$-alkylcarbonyl;

B is
hydrogen, $C_1$–$C_6$-alkyl, $C_3$–$C_6$-alkenyl, $C_3$–$C_6$-alkynyl, $C_1$–$C_6$-haloalkyl, $C_3$–$C_8$-cycloalkyl —O$R^{16}$ or —S$R^{16}$, where $R^{16}$ is
hydrogen, $C_1$–$C_6$-alkyl, $C_3$–$C_6$-alkenyl, $C_3$–$C_6$-alkynyl, $C_3$–$C_8$-cycloalkyl, $C_2$–$C_6$-haloalkyl, phenyl which may be unsubstituted or may be substituted by one to three radicals selected from the group consisting of $C_1$–$C_6$-alkyl, $C_2$–$C_6$-alkenyl, halogen, cyano, nitro, $C_1$–$C_6$-alkoxy and $C_1$–$C_6$-alkoxycarbonyl, $C_1$–$C_6$-cyanoalkyl, $C_3$–$C_6$-haloalkenyl, $C_1$–$C_6$-alkoxycarbonyl, $C_1$–$C_6$-alkoxy-$C_1$–$C_6$-alkyl, $C_1$–$C_6$-alkoxycarbonyl-$C_1$–$C_6$-alkyl or $C_1$–$C_6$-alkoximino-$C_1$–$C_6$-alkyl;

phenyl which may be unsubstituted or may be substituted by one to three radicals selected from the group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl;

—$NR^8R^9$, where $R^8$ and $R^9$ independently of one another are hydrogen, $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl or phenyl which may be unsubstituted or may be substituted by one to three radicals selected from the group consisting of $C_1$–$C_6$-alkyl, $C_2$–$C_6$-alkenyl, halogen, cyano, nitro, $C_1$–$C_6$-alkoxy and $C_1$–$C_8$-alkoxycarbonyl, or where $R^8$ and $R^9$, together with the common nitrogen atom, form a saturated or partially or completely unsaturated 4- to 7-membered ring which may additionally contain one or two further heteroatoms as ring members, selected from the group consisting of nitrogen, oxygen and sulfur;

$C_1$–$C_6$-alkoxy-$C_1$–$C_6$-alkyl, di-($C_1$–$C_6$-alkoxy)-$C_1$–$C_6$-alkyl, $C_1$–$C_6$-alkylthio-$C_1$–$C_6$-alkyl;

$R^{10}$ is
hydrogen or cyano
$C_1$–$C_6$-alkyl, $C_3$–$C_6$-alkenyl, $C_3$–$C_6$-alkynyl,
$C_1$–$C_6$-haloalkyl,
$C_3$–$C_8$-cycloalkyl,
$C_1$–$C_6$-alkoxycarbonyl,
$C_1$–$C_6$-alkoxycarbonyl-$C_1$–$C_6$-alkyl, $R^{11}$ is
hydrogen, $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl,
phenyl which may be unsubstituted or may optionally be substituted by one to three radicals selected from the group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl,
$C_1$–$C_6$-alkoxy-$C_1$–$C_6$-alkyl, hydroxyl,
$C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_8$-cycloalkyl-$C_1$–$C_6$-alkoxy,
$C_1$–$C_6$-alkylcarbonyloxy,
$C_1$–$C_6$-cyanoalkoxy, $C_1$–$C_6$-alkoxy-$C_1$–$C_6$-alkoxy, $C_1$–$C_6$-alkoxycarbonyl-$C_1$–$C_6$-alkoxy, hydroxy-$C_1$–$C_6$-alkoxy, $C_1$–$C_6$-alkylthio-$C_1$–$C_6$-alkoxy, $C_1$–$C_6$-alkylamino-$C_1$–$C_6$-alkoxy, di-($C_1$–$C_6$-alkyl)-amino-$C_1$–$C_6$-alkoxy,
phenyl-$C_1$–$C_6$-alkoxy, phenyl-$C_3$–$C_6$-alkenyloxy or phenyl-$C_3$–$C_6$-alkynyloxy, where in each case one or two methylene groups of the alkoxy, alkenyloxy and alkynyloxy chains may be replaced by oxygen, sulfur and/or a $C_1$–$C_6$-alkylamino chain, and where the phenyl ring may be unsubstituted or may optionally be substituted by one to three substituents selected from the group consisting of $C_1$–$C_6$-alkyl, $C_2$–$C_6$-alkenyl, halogen, cyano, nitro, $C_1$–$C_6$-alkoxy and $C_1$–$C_6$-alkoxycarbonyl,

—$NR^8R^9$;

$R^{12}$ and $R^{13}$ are
$C_1$–$C_6$-alkoxy or phenyl which may be unsubstituted or may optionally be substituted by one to three radicals selected from the group consisting of $C_1$–$C_6$-alkyl, $C_1$–$C_6$-haloalkyl, $C_3$–$C_6$-alkenyl, halogen, cyano, nitro, $C_1$–$C_6$-alkoxy and $C_1$–$C_6$-alkoxy-carbonyl; $X^1$ and $X^2$ are oxygen or sulfur;

$R^{14}$ and $R^{15}$ are
$C_1$–$C_6$-alkyl, $C_3$–$C_6$-alkenyl, $C_3$–$C_6$-alkynyl or $C_1$–$C_6$-alkoxy-$C_1$–$C_6$-alkyl or $R^{14}$ and $R^{15}$ together are a two- to four-membered carbon chain which may be unsaturated and which, optionally, may contain a carbonyl group as a chain member,
where the carbon chain may be unsubstituted or may optionally be substituted by one to three radicals selected from the group consisting of $C_1$–$C_6$-alkyl, $C_2$–$C_6$-alkenyl, halogen, cyano, nitro, amino, $C_1$–$C_6$-alkoxy, $C_3$–$C_6$-alkenyloxy, $C_3$–$C_6$-alkynyloxy, carboxyl, $C_1$–$C_6$-alkoxycarbonyl, $C_1$–$C_6$-haloalkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-hydroxyalkyl and $C_1$–$C_6$-cyanoalkyl;

or $R^5$ and $R^6$
together are a saturated or partially or completely unsaturated three- to five-membered carbon chain which, optionally, may contain one or two oxygen, sulfur or nitrogen atoms and/or a carbonyl group as a chain member, and where the chain may be unsubstituted or may optionally be substituted by one or two radicals selected from the group consisting of cyano, nitro, amino, halogen, $C_1$–$C_6$-alkyl, $C_1$–$C_6$-haloalkyl, $C_2$–$C_6$-alkenyl, $C_3$–$C_6$-alkynyl, $C_1$–$C_6$-cyanoalkyl, $C_1$–$C_6$-alkoxycarbonyl-$C_1$–$C_6$-alkyl, phenyl-$C_1$–$C_6$-alkyl and 3- to 8-membered heterocyclyl-$C_1$–$C_6$-alkyl, where the heterocycle may in turn be saturated or partially or completely unsaturated and may optionally contain one to four heteroatoms selected from the group consisting of one to four nitrogen atoms, one or two oxygen atoms and one or two sulfur atoms;

excluding those compounds of formula I in which $R^1$ and $R^2$ are hydrogen and $R^5$ and $R^6$ together form a substituted chain —CH═CH—NH— and excluding those compounds of formula I in which $R^1$ and $R^2$ are hydrogen and $R^4$ is fluorine and $R^5$ and $R^6$ together are a substituted chain —O—$CH_2$—CO—NH—, and the agriculturally utilizable salts of the compounds of formula I.

2. A compound of the formula I as defined in claim 1, wherein $R^1$ and $R^2$ are hydrogen, $C_1$–$C_6$-alkyl, $C_2$–$C_6$-alkenyl, $C_1$–$C_6$-alkoxy-$C_1$–$C_6$-alkyl, ($C_1$–$C_6$-alkoxy)carbonyl or ($C_1$–$C_6$-alkyl)carbonyl;

$R^5$ is hydrogen, cyano or halogen;

$R^6$ is —A—CO—B, —$C(R^{10})$═O OR —$C(R^{10})$═N—$R^{11}$, where

A is a $C_1$–$C_4$-alkylene, $C_2$–$C_4$-alkenylene or $C_2$–$C_4$-alkynylene chain which in each case is unsubstituted or may optionally be substituted by one or two radicals selected from the group consisting of halogen, $C_1$–$C_6$-alkyl, ($C_1$–$C_6$-alkoxy)carbonyl and ($C_1$–$C_6$-alkyl)carbonyl;

B is —$OR^{16}$ or —$NR^8R^9$, and $R^{11}$ is $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_8$-cycloalkyl-$C_1$–$C_6$-alkoxy, ($C_1$–$C_6$-alkoxy)carbonyl-$C_1$–$C_6$-alkoxy or —$NR^8R^9$.

3. A compound of the formula I as defined in claim 1, wherein $R^1$ and $R^2$ are hydrogen, $C_1$–$C_6$-alkyl, $C_2$–$C_6$-alkenyl, $C_1$–$C_6$-alkoxy-$C_1$–$C_6$-alkyl or ($C_1$–$C_6$-alkyl)carbonyl;

$R^3$ is hydrogen;

$R^4$ is hydrogen or fluorine;

$R^5$ is cyano or chlorine;

$R^6$ is a group —A—CO—B, —$C(R^{10})$=O or —$C(R^{10})$=N—$R^{11}$, where

A is a $C_1$–$C_4$-alkylene chain which is unsubstituted or may optionally be substituted by one or two radicals selected from the group consisting of halogen, $C_1$–$C_6$-alkyl, ($C_1$–$C_6$-alkoxy)carbonyl and ($C_1$–$C_6$-alkyl)carbonyl; B is —$OR^{16}$; and $R^{11}$ is $C_1$–$C_6$-alkyl, $C_3$–$C_6$-alkenyl, $C_3$–$C_6$-alkynyl, $C_3$–$C_8$-cycloalkyl, $C_1$–$C_6$-haloalkyl, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_6$-cycloalkyl-$C_1$–$C_6$-alkoxy, ($C_1$–$C_6$-alkoxy)carbonyl-$C_1$–$C_6$-alkoxy or —$NR^8R^9$.

4. A substituted hydroxyisoindolone of the formula II

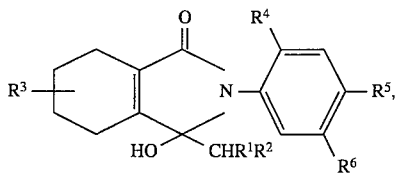

in which the variables have the meanings given in claim 1, for the compounds of formula I and the agriculturally utilizable salts of the compounds II.

5. A herbicidal composition containing an inert liquid or solid carrier and a herbicidally active amount of at least one substituted isoindolone compound of the formula I as defined in claim 1 or an agriculturally utilizable salt of a compound of formula I.

6. A composition for desiccating and/or defoliating plants, containing, in addition to customary additives, an amount of at least one substituted isoindolone compound of the formula I having desiccant and/or defoliant activity or an agriculturally utilizable salt of a compound of formula I as defined in claim 1.

7. A method for controlling undesired plant growth, which comprises allowing a herbicidally active amount of at least one substituted isoindolone compound of the formula I or an agriculturally utilizable salt of a compound of formula I as defined in claim 1 to act on plants or their environment or on seeds.

8. A method for desiccating and/or defoliating plants, which comprises allowing an effective amount of a composition which has desiccant and/or defoliant activity as defined in claim 6 to act on the plants.

9. A herbicidal composition containing an inert liquid or solid carrier and an amount of at least one hydroxyisoindolone compound of the formula II as defined in claim 4 having herbicidal activity or an agriculturally utilizable salt of a compound of the formula II as defined in claim 4.

10. A composition for desiccating and/or defoliating plants, containing, in addition to customary additives, an amount of at least one hydroxyisoindolone compound of the formula II as defined in claim 4 having desiccant and/or defoliant activity or an agriculturally utilizable salt of a compound of the formula II as defined in claim 4.

11. A method for controlling undesired plant growth, which comprises allowing an amount of at least one hydroxyisoindolone compound of the formula II as defined in claim 4 having herbicidal activity or an agriculturally utilizable salt of a compound of the formula II as defined in claim 4 to act on plants or their environment or on seeds.

12. A method for desiccating and/or defoliating plants, which comprises allowing an effective amount of a composition having desiccant or defoliant activity as defined in claim 10 to act on the plants.

* * * * *